(12) United States Patent
Samoylova et al.

(10) Patent No.: US 11,666,624 B2
(45) Date of Patent: Jun. 6, 2023

(54) PHAGE-PEPTIDE CONSTRUCTS FOR STIMULATING AN IMMUNE RESPONSE AGAINST CD47

(71) Applicants: Auburn University, Auburn, AL (US); Edward Via College of Osteopathic Medicine—Auburn, Auburn, AL (US)

(72) Inventors: Tatiana I. Samoylova, Auburn, AL (US); Alexandre M. Samoylov, Auburn, AL (US); Kenny V. Brock, Auburn, AL (US); Anna M. Cochran, Auburn, AL (US); James W. Gillespie, Auburn, AL (US)

(73) Assignees: Auburn University, Auburn, AL (US); Edward Via College of Osteopathic Medicine—Auburn, Auburn, AL (US)

( * ) Notice: Subject to any disclaimer, the term of this patent is extended or adjusted under 35 U.S.C. 154(b) by 77 days.

(21) Appl. No.: 17/031,663

(22) Filed: Sep. 24, 2020

(65) Prior Publication Data
US 2021/0085750 A1  Mar. 25, 2021

Related U.S. Application Data

(60) Provisional application No. 62/976,113, filed on Feb. 13, 2020, provisional application No. 62/905,057, filed on Sep. 24, 2019.

(51) Int. Cl.
*A61K 38/10* (2006.01)
*A61K 47/50* (2017.01)
(Continued)

(52) U.S. Cl.
CPC .............. *A61K 38/10* (2013.01); *A61K 38/08* (2013.01); *A61K 47/6901* (2017.08);
(Continued)

(58) Field of Classification Search
None
See application file for complete search history.

(56) References Cited

U.S. PATENT DOCUMENTS

| 4,458,066 A | 7/1984 | Caruthers |
| 4,683,195 A | 7/1987 | Mullis |
| (Continued) |

OTHER PUBLICATIONS

Brigati, J. R., et al. "Phage display for generating peptide reagents." Current protocols in protein science 51.1 (2008): 18-9.
(Continued)

*Primary Examiner* — Kevin S Orwig
(74) *Attorney, Agent, or Firm* — Quarles & Brady, LLP

(57) ABSTRACT

Disclosed are recombinant bacteriophage constructs and related exogenous peptide sequences for generating immune responses against CD47. The disclosed recombinant phage constructs bind to antibodies against CD47 and can be administered to an animal to generate an immune response against CD47, including generating anti-CD47 antibodies. The disclosed recombinant phage may comprise an amino acid sequence of CD47, epitopic fragments, variants, or functional mimics thereof. Also disclosed are methods for making and selecting such recombinant phage constructs and compositions that comprise such constructs (e.g., compositions for inducing an immune response against CD47 including pharmaceutical or veterinary compositions used as vaccines). Also disclosed are recombinant polynucleotides comprising genomic nucleic acid of the recombinant phage constructs disclosed herein.

19 Claims, 19 Drawing Sheets
Specification includes a Sequence Listing.

(51) Int. Cl.
*C07K 7/06* (2006.01)
*A61P 35/00* (2006.01)
*A61K 38/08* (2019.01)
*A61K 47/69* (2017.01)
*C07K 7/08* (2006.01)

(52) U.S. Cl.
CPC ............. *A61P 35/00* (2018.01); *C07K 7/06* (2013.01); *C07K 7/08* (2013.01)

(56) References Cited

U.S. PATENT DOCUMENTS

| | | | |
|---|---|---|---|
| 4,683,202 | A | 7/1987 | Mullis |
| 5,494,810 | A | 2/1996 | Barany |
| 6,383,496 | B1 | 5/2002 | Curtiss |
| 6,923,958 | B2 | 8/2005 | Xiang |
| 7,094,868 | B2 | 8/2006 | Samoylova |
| 7,396,664 | B2 | 7/2008 | Daly |
| 7,642,063 | B2 | 1/2010 | Samoylova |
| 8,057,992 | B2 | 11/2011 | Samoylova |
| 8,158,366 | B2 | 4/2012 | Samoylova |
| 8,492,516 | B2 | 7/2013 | Samoylova |
| 8,871,901 | B2 | 10/2014 | Samoylova |
| 2003/0216322 | A1 | 11/2003 | Samoylova |
| 2004/0031072 | A1 | 2/2004 | La Rosa |
| 2004/0147731 | A1 | 7/2004 | Parkos |
| 2005/0260133 | A1 | 11/2005 | Samoylova |
| 2009/0280137 | A1 | 11/2009 | Samoylova |
| 2010/0111995 | A1 | 5/2010 | Bachman |
| 2011/0044989 | A1 | 2/2011 | Samoylova |
| 2011/0311565 | A1 | 12/2011 | Samoylova |
| 2012/0156215 | A1 | 6/2012 | Samoylova |
| 2012/0164165 | A1 | 6/2012 | Samoylova |
| 2013/0039972 | A1 | 2/2013 | Pasqualini |
| 2014/0030283 | A1 | 1/2014 | Samoylova |
| 2017/0340684 | A1 | 11/2017 | Hajitou |
| 2018/0311343 | A1 | 11/2018 | Huang |
| 2021/0085750 | A1 | 3/2021 | Samoylova |

OTHER PUBLICATIONS

Cheever, M. A. "Twelve immunotherapy drugs that could cure cancers." Immunological reviews 222.1 (2008): 357-368.

Eriksson, F., et al. "Tumor specific phage particles promote tumor regression in a mouse melanoma model." Cancer Immunology, immunotherapy 56.5 (2007): 677-687.

Eriksson, F., et al. "Tumor-specific bacteriophages induce tumor destruction through activation of tumor-associated macrophages." The Journal of Immunology 182.5 (2009): 3105-3111.

International Searching Authority. International Search Report and Written Opinion for application PCT/US2020/052557, dated Jan. 19, 2021. 13 pages.

Kojima, Y., et al. "CD47-blocking antibodies restore phagocytosis and prevent atherosclerosis." Nature 536.7614 (2016): 86-90.

Krag, D. N., et al. "Selection of tumor-binding ligands in cancer patients with phage display libraries." Cancer research 66.15 (2006): 7724-7733.

Petrenko, V. A., et al. "A library of organic landscapes on filamentous phage." Protein Engineering, Design and Selection 9.9 (1996): 797-801.

Samoylov, A., et al. "Generation and Characterization of Phage-Gn RH Chemical Conjugates for Potential Use in Cat and Dog Immunocontraception." Reproduction in Domestic Animals 47 (2012): 406-411.

Samoylov, A., et al. "Humoral immune responses against gonadotropin releasing hormone elicited by immunization with phage-peptide constructs obtained via phage display." Journal of biotechnology 216 (2015): 20-28.

Samoylova, T. I., et al. "Infective and inactivated filamentous phage as carriers for immunogenic peptides." Journal of virological methods 183.1 (2012): 63-68.

Samoylova, T. I., et al. "Phage display allows identification of zona pellucida-binding peptides with species-specific properties: novel approach for development of contraceptive vaccines for wildlife." Journal of Biotechnology 162.2-3 (2012): 311-318.

Samoylova, T. I., et al. "ZP-binding peptides identified via phage display stimulate production of sperm antibodies in dogs." Animal reproduction science 120.1-4 (2010): 151-157.

Weiskopf, K., "Cancer immunotherapy targeting the CD47/SIRPa axis." European journal of cancer 76 (2017): 100-109.

Weiskopf, K., et al. (2016). Eradication of canine diffuse large B-cell lymphoma in a murine xenograft model with CD47 blockade and anti-CD20. Cancer immunology research, 4(12), 1072-1087.

Willingham, S. B., et al. "The CD47-signal regulatory protein alpha (SIRPa) interaction is a therapeutic target for human solid tumors." Proceedings of the National Academy of Sciences 109.17 (2012): 6662-6667.

Yip, Y. L., et al. "Comparison of phage pIII, pVIII and GST as carrier proteins for peptide immunisation in Balb/c mice." Immunology letters 79.3 (2001): 197-202.

| Sample | Target | Library | Fraction | Total Reads | Cutadapt Sense Reads | Sense (%) | Cutadapt Anti-sense Reads | Anti-sense (%) | Total Reads | Total (%) | Post Read Length | Unique Pep Q>33 |
|---|---|---|---|---|---|---|---|---|---|---|---|---|
| 1 | BRIC126 | PhD-12mer | Elution | 2,636,278 | 1,175,980 | 44.6 | 1,100,022 | 41.7 | 2,276,002 | 86.33 | 36.0 | 11,912 |
| 2 | BRIC126 | PhD-12mer | Post-Elution | 3,144,242 | 1,344,513 | 42.8 | 1,249,507 | 39.7 | 2,594,020 | 82.50 | 36.0 | 10,347 |
| 3 | B6H12 | PhD-12mer | Elution | 3,310,361 | 1,432,708 | 43.3 | 1,503,822 | 45.4 | 2,936,530 | 88.71 | 36.0 | 19,134 |
| 4 | B6H12 | PhD-12mer | Post-Elution | 2,239,073 | 964,426 | 43.1 | 1,001,804 | 44.7 | 1,966,230 | 87.81 | 36.0 | 17,229 |
| 5 | BRIC126 | PhD-7mer | Elution | 2,538,357 | 1,125,550 | 44.3 | 1,169,022 | 46.1 | 2,294,572 | 90.40 | 21.0 | 26,520 |
| 6 | BRIC126 | PhD-7mer | Post-Elution | 2,729,719 | 1,067,001 | 39.1 | 1,109,550 | 40.6 | 2,176,551 | 79.74 | 21.0 | 23,159 |
| Average | | | | 2,766,338 | 1,185,030 | 42.9 | 1,188,955 | 43.0 | 2,373,984 | 85.91 | 31.0 | 18,050 |
| Stdev.S | | | | 396,740 | 174,926 | 2.0 | 174,611 | 2.7 | 342,352 | 4.04 | 7.7 | 6,272 |
| Total | | | | 16,598,030 | 7,110,178 | | 7,133,727 | | 14,243,905 | | | 108,301 |

FIG. 11

SEQUENCE LISTING

```
<160> NUMBER OF SEQ ID NOS: 54

<210> SEQ ID NO 1
<211> LENGTH: 11
<212> TYPE: PRT
<213> ORGANISM: Artificial Sequence
<220> FEATURE:
<223> OTHER INFORMATION: Synthetic- peptide-based antigen mimic

<400> SEQUENCE: 1

Gly Leu Ser Asp Tyr Tyr Arg Ala Leu Ala Asn
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 2

Gly Ile Thr Glu Tyr Leu Arg Thr Ile Asn Ile Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 3

Asp Tyr Ser Leu Arg Leu Gln Tyr Gly His Thr Tyr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic- peptide-based antigen mimic

<400> SEQUENCE: 4

Gly Leu Thr Asp Tyr Leu Gly
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic- peptide-based antigen mimic
```

```
<400> SEQUENCE: 5

Glu Tyr Val Ala Pro Phe Asn Phe Leu Glu Trp Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 6

Tyr Ser Asp Thr Ser Leu Ser Tyr Met Gln Arg Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 7

Gly Leu Gly Asp Arg Leu Ser His Gly His Thr Ile
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 8

Asp Tyr Ser Leu Arg Leu Gln Tyr Gly His Thr Tyr Gly Gly Gly Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 9

Glu Tyr Val Ala Pro Phe Asn Phe Leu Glu Trp Lys Gly Gly Gly Ser
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 10

Gly Ile Ser Asp Tyr Ile Gly Gly Lys His His Val Gly Gly Gly Ser
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 11
```

Gly Ile Thr Asp Phe Leu Ser Trp Ser Trp Gln Ala Gly Gly Gly Ser
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 12

Gly Ile Thr Glu Tyr Leu Arg Thr Ile Asn Ile Gly Gly Gly Gly Ser
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic- peptide-based antigen mimic

<400> SEQUENCE: 13

Gly Lys Leu Ala Asn Ile Ala Gly Gly Gly Ser
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 14

Gly Leu Ser Asp Tyr Tyr Tyr Arg Ala Leu Ala Asn Gly Gly Gly Ser
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Synthetic- peptide-based antigen mimic

<400> SEQUENCE: 15

Gly Leu Thr Asp Tyr Leu Gly Gly Gly Gly Ser
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 16

Tyr Ser Asp Thr Ser Leu Ser Tyr Met Gln Arg Tyr Gly Gly Gly Ser
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 17

Gly Ile Thr Glu Tyr Leu Arg Thr Ile Asn Ile Gly Gly Gly Gly Ser
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Synthetic- peptide-based antigen mimic

<400> SEQUENCE: 18

Gly Ile Thr Glu Tyr Leu Arg Thr Ile Asn Ile Gly Lys
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Synthetic- peptide-based antigen mimic

<400> SEQUENCE: 19

Gly Ile Thr Glu Tyr Leu Arg Thr Ile Asn Ile Gly Gly Gly Gly Ser
1               5                   10                  15

Lys

<210> SEQ ID NO 20
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 20

Gly Ile Asn Ile Thr Arg Leu Tyr Glu Thr Ile Gly
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 21

Ser Gly Gly Gly Gly Ile Asn Ile Thr Arg Leu Tyr Glu Thr Ile Gly
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Synthetic- peptide-based antigen mimic

<400> SEQUENCE: 22

Gly Ile Thr Glu Tyr Leu Arg Thr Ile Gly Leu Ser Asp Tyr Tyr Tyr
1               5                   10                  15

Arg Ala

<210> SEQ ID NO 23
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 23

Gly Leu Ser Asp Tyr Tyr Tyr Arg Ala Leu Ala Asn
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 24

Gly Leu Ser Asp Tyr Tyr Tyr Arg Ala Leu Ala Asn Gly Gly Gly Ser
1               5                   10                  15

<210> SEQ ID NO 25
<211> LENGTH: 13
<212> TYPE: PRT
<213> ORGANISM: Artificial Sequence
<220> FEATURE:
<223> OTHER INFORMATION: Synthetic- peptide-based antigen mimic

<400> SEQUENCE: 25

Gly Leu Ser Asp Tyr Tyr Tyr Arg Ala Leu Ala Asn Lys
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic- peptide-based antigen mimic

<400> SEQUENCE: 26

Gly Leu Ser Asp Tyr Tyr Tyr Arg Ala Leu Ala Asn Gly Gly Gly Ser
1               5                   10                  15

Lys

<210> SEQ ID NO 27
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 27

Asn Ala Leu Ala Arg Tyr Tyr Tyr Asp Ser Leu Gly
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 28

Ser Gly Gly Gly Asn Ala Leu Ala Arg Tyr Tyr Tyr Asp Ser Leu Gly
1               5                   10                  15

<210> SEQ ID NO 29
<211> LENGTH: 16
<212> TYPE: PRT
<213> ORGANISM: Artificial Sequence
<220> FEATURE:

<223> OTHER INFORMATION: Synthetic- peptide-based antigen mimic

<400> SEQUENCE: 29

Asp Tyr Ser Leu Arg Leu Gln Tyr Gly His Thr Tyr Gly Gly Gly Ser
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: Synthetic- peptide-based antigen mimic

<400> SEQUENCE: 30

Asp Tyr Ser Leu Arg Leu Gln Tyr Gly His Thr Tyr Lys
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Synthetic- peptide-based antigen mimic

<400> SEQUENCE: 31

Asp Tyr Ser Leu Arg Leu Gln Tyr Gly His Thr Tyr Gly Gly Gly Ser
1               5                   10                  15

Lys

<210> SEQ ID NO 32
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 32

Tyr Thr His Gly Tyr Gln Leu Arg Leu Ser Tyr Asp
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic- peptide-based antigen mimic

<400> SEQUENCE: 33

Ser Gly Gly Gly Tyr Thr His Gly Tyr Gln Leu Arg Leu Ser Tyr Asp
1               5                   10                  15

<210> SEQ ID NO 34
<211> LENGTH: 8
<212> TYPE: PRT
<213> ORGANISM: Artificial Sequence
<220> FEATURE:
<223> OTHER INFORMATION: Synthetic- peptide-based antigen mimic

<400> SEQUENCE: 34

Gly Leu Thr Asp Tyr Leu Gly Cys
1               5

<210> SEQ ID NO 35
<211> LENGTH: 12
<212> TYPE: PRT
<213> ORGANISM: Artificial Sequence

```
<220> FEATURE:
<223> OTHER INFORMATION: Synthetic- peptide-based antigen mimic

<400> SEQUENCE: 35

Gly Leu Thr Asp Tyr Leu Gly Gly Gly Ser Cys
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic- peptide-based antigen mimic

<400> SEQUENCE: 36

Gly Ile Thr Glu Tyr Leu Arg Thr Ile Asn Ile Gly Cys
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Synthetic- peptide-based antigen mimic

<400> SEQUENCE: 37

Gly Ile Thr Glu Tyr Leu Arg Thr Ile Asn Ile Gly Gly Gly Gly Ser
1               5                   10                  15

Cys

<210> SEQ ID NO 38
<211> LENGTH: 13
<212> TYPE: PRT
<213> ORGANISM: Artificial Sequence
<220> FEATURE:
<223> OTHER INFORMATION: Synthetic- peptide-based antigen mimic

<400> SEQUENCE: 38

Gly Leu Ser Asp Tyr Tyr Tyr Arg Ala Leu Ala Asn Cys
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Synthetic- peptide-based antigen mimic

<400> SEQUENCE: 39

Gly Leu Ser Asp Tyr Tyr Tyr Arg Ala Leu Ala Asn Gly Gly Gly Ser
1               5                   10                  15

Cys

<210> SEQ ID NO 40
<211> LENGTH: 13
<212> TYPE: PRT
<213> ORGANISM: Artificial Sequence
<220> FEATURE:
<223> OTHER INFORMATION: Synthetic- peptide-based antigen mimic

<400> SEQUENCE: 40

Asp Tyr Ser Leu Arg Leu Gln Tyr Gly His Thr Tyr Cys
1               5                   10

<210> SEQ ID NO 41
```

```
<211> LENGTH: 17
<212> TYPE: PRT
<213> ORGANISM: Artificial Sequence
<220> FEATURE:
<223> OTHER INFORMATION: Synthetic- peptide-based antigen mimic

<400> SEQUENCE: 41

Asp Tyr Ser Leu Arg Leu Gln Tyr Gly His Thr Tyr Gly Gly Gly Ser
1               5                   10                  15

Cys

<210> SEQ ID NO 42
<211> LENGTH: 305
<212> TYPE: PRT
<213> ORGANISM: Homo sapiens

<400> SEQUENCE: 42

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
            50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
            130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Asn
        290                 295                 300

Asn
```

```
<210> SEQ ID NO 43
<211> LENGTH: 303
<212> TYPE: PRT
<213> ORGANISM: Canis lupus

<400> SEQUENCE: 43

Met Trp Pro Leu Ala Ala Leu Leu Leu Gly Ser Ala Ser Cys Gly
1               5                   10                  15

Ser Ala Gln Leu Ile Phe Asn Ile Thr Lys Ser Val Glu Tyr Thr Ala
                20                  25                  30

Cys Asn Glu Ser Ala Ile Ile Pro Cys Phe Val Asn Val Glu Ala
            35                  40                  45

Thr Asn Ile Asn Glu Met Tyr Val Lys Trp Lys Phe Arg Gly Lys Asp
        50                  55                  60

Ile Phe Thr Phe Asp Gly Ala Val Gln Lys Thr Thr His Gly Asp Lys
65                  70                  75                  80

Phe Lys Ser Thr Lys Ile Val Pro Gln Lys Leu Leu Asn Gly Ile Ala
                85                  90                  95

Ser Leu Glu Met Ser Lys Glu Glu Ala Val Val Gly Asn Tyr Thr Cys
            100                 105                 110

Glu Val Thr Glu Leu Ser Arg Glu Gly Glu Thr Ile Ile Glu Leu Lys
        115                 120                 125

Tyr Arg Ile Val Ser Trp Phe Ser Pro Asn Glu Asn Ile Leu Ile Val
    130                 135                 140

Ile Phe Pro Ile Leu Ala Val Leu Leu Ser Trp Gly Gln Phe Gly Ile
145                 150                 155                 160

Val Thr Ile Lys Tyr Lys Ser Ser Ile Met Lys Glu Lys Thr Ile Phe
                165                 170                 175

Leu Phe Val Gly Gly Leu Val Leu Thr Ile Val Val Ile Val Gly Ala
            180                 185                 190

Ile Leu Phe Val Pro Gly Glu Tyr Ser Thr Lys Asn Ser Cys Gly Leu
        195                 200                 205

Gly Leu Ile Val Ile Pro Thr Val Ile Leu Thr Leu Leu Gln Tyr Cys
    210                 215                 220

Val Phe Met Ile Gly Val Trp Met Ser Pro Phe Thr Ile Ala Ile Leu
225                 230                 235                 240

Ile Leu Gln Val Leu Gly Tyr Val Leu Ser Val Val Gly Leu Ser Leu
                245                 250                 255

Cys Val Ser Glu Cys Thr Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Leu Val Ala Ser Asn Gln Lys Thr Ile Gln Pro Pro Arg Ser Asn
    290                 295                 300

<210> SEQ ID NO 44
<211> LENGTH: 303
<212> TYPE: PRT
<213> ORGANISM: Mus musculus

<400> SEQUENCE: 44

Met Trp Pro Leu Ala Ala Ala Leu Leu Leu Gly Ser Cys Cys Gly
1               5                   10                  15

Ser Ala Gln Leu Leu Phe Ser Asn Val Asn Ser Ile Glu Phe Thr Ser
```

```
                20                  25                  30
Cys Asn Glu Thr Val Val Ile Pro Cys Ile Val Arg Asn Val Glu Ala
             35                  40                  45
Gln Ser Thr Glu Glu Met Phe Val Lys Trp Lys Leu Asn Lys Ser Tyr
         50                  55                  60
Ile Phe Ile Tyr Asp Gly Asn Lys Asn Ser Thr Thr Asp Gln Asn
 65                  70                  75                  80
Phe Thr Ser Ala Lys Ile Ser Val Ser Asp Leu Ile Asn Gly Ile Ala
                 85                  90                  95
Ser Leu Lys Met Asp Lys Arg Asp Ala Met Val Gly Asn Tyr Thr Cys
                100                 105                 110
Glu Val Thr Glu Leu Ser Arg Glu Gly Lys Thr Val Ile Glu Leu Lys
                115                 120                 125
Asn Arg Thr Val Ser Trp Phe Ser Pro Asn Glu Lys Ile Leu Ile Val
                130                 135                 140
Ile Phe Pro Ile Leu Ala Ile Leu Leu Phe Trp Gly Lys Phe Gly Ile
145                 150                 155                 160
Leu Thr Leu Lys Tyr Lys Ser Ser His Thr Asn Lys Arg Ile Ile Leu
                165                 170                 175
Leu Leu Val Ala Gly Leu Val Leu Thr Val Ile Val Val Gly Ala
                180                 185                 190
Ile Leu Leu Ile Pro Gly Glu Lys Pro Val Lys Asn Ala Ser Gly Leu
                195                 200                 205
Gly Leu Ile Val Ile Ser Thr Gly Ile Leu Ile Leu Leu Gln Tyr Asn
                210                 215                 220
Val Phe Met Thr Ala Phe Gly Met Thr Ser Phe Thr Ile Ala Ile Leu
225                 230                 235                 240
Ile Thr Gln Val Leu Gly Tyr Val Leu Ala Leu Val Gly Leu Cys Leu
                245                 250                 255
Cys Ile Met Ala Cys Glu Pro Val His Gly Pro Leu Leu Ile Ser Gly
                260                 265                 270
Leu Gly Ile Ile Ala Leu Ala Glu Leu Leu Gly Leu Val Tyr Met Lys
                275                 280                 285
Phe Val Ala Ser Asn Gln Arg Thr Ile Gln Pro Pro Arg Asn Arg
                290                 295                 300
```

<210> SEQ ID NO 45
<211> LENGTH: 303
<212> TYPE: PRT
<213> ORGANISM: Rattus norvegicus

<400> SEQUENCE: 45

```
Met Trp Pro Leu Ala Ala Ala Leu Leu Leu Gly Ser Cys Cys Cys Gly
 1               5                  10                  15
Ser Ala Gln Leu Leu Leu Ser Lys Val Lys Ser Val Glu Phe Thr Ser
                20                  25                  30
Cys Asn Asp Thr Val Val Ile Pro Cys Lys Val Leu Asn Val Glu Ala
                 35                  40                  45
Gln Ser Thr Asp Glu Met Phe Val Lys Trp Lys Leu Asn Lys Ser Tyr
         50                  55                  60
Ile Phe Ile Tyr Asp Gly Asn Lys Asn Ser Thr Thr Arg Glu Gln Asn
 65                  70                  75                  80
Phe Thr Ser Ala Lys Ile Ser Val Ser Asp Leu Leu Lys Gly Ile Ala
                 85                  90                  95
```

Ser Leu Thr Met Asp Thr His Glu Ala Val Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Pro Val Ser Trp Phe Ser Thr Asn Glu Lys Ile Leu Ile Val
130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Ala Leu Thr Leu Ile Val Val Gly Ala
                180                 185                 190

Ile Leu Phe Ile Pro Gly Glu Lys Pro Val Lys Asn Ala Ser Gly Leu
            195                 200                 205

Gly Leu Ile Val Ile Ser Thr Gly Ile Leu Ile Leu Leu Gln Tyr Asn
        210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Val Val Gly Met Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Arg Asn Asn
290                 295                 300

<210> SEQ ID NO 46
<211> LENGTH: 303
<212> TYPE: PRT
<213> ORGANISM: Bos taurus

<400> SEQUENCE: 46

Met Trp Pro Leu Val Val Leu Leu Leu Gly Ser Val Arg Cys Gly
1               5                   10                  15

Ser Ala Gln Leu Ile Phe Asn Ala Ile Lys Ser Val Glu Tyr Thr Leu
            20                  25                  30

Cys Asn Gln Thr Val Val Ile Pro Cys Phe Val Asn Asn Val Glu Thr
        35                  40                  45

Lys Asn Ile Thr Glu Leu Tyr Val Arg Trp Lys Phe Lys Gly Glu Asn
    50                  55                  60

Ile Phe Ile Phe Asp Gly Ser Gln Arg Met Ser Lys Pro Ser Ser Asn
65                  70                  75                  80

Phe Ser Ser Ala Glu Ile Ala Pro Ser Glu Leu Leu Arg Gly Ile Ala
                85                  90                  95

Ser Leu Lys Met Ala Lys Ser Asp Ala Val Leu Gly Asn Tyr Thr Cys
            100                 105                 110

Glu Val Thr Glu Leu Ser Arg Glu Gly Glu Thr Ile Ile Glu Leu Lys
        115                 120                 125

Tyr Arg Val Val Ser Trp Phe Ser Pro Asn Glu Asn Ile Leu Ile Val
130                 135                 140

Ile Phe Pro Val Leu Ala Ile Leu Leu Phe Trp Gly Gln Phe Gly Ile
145                 150                 155                 160

Val Thr Leu Lys Tyr Lys Ser Asn Tyr Thr Lys Glu Lys Ala Ile Phe
                165                 170                 175

```
Leu Leu Val Ala Gly Leu Leu Thr Val Leu Val Ile Val Gly Ala
            180                 185                 190

Phe Leu Phe Ile Pro Gly Gly Tyr Ser Thr Lys Asn Ala Ser Gly Leu
        195                 200                 205

Gly Leu Ile Val Leu Pro Thr Ile Ile Leu Ile Leu Leu His Tyr Cys
    210                 215                 220

Val Phe Met Ile Ala Met Gly Met Ser Ser Phe Thr Ile Ser Ile Leu
225                 230                 235                 240

Ile Leu Gln Leu Leu Gly Tyr Val Leu Ser Val Val Gly Phe Ser Leu
                245                 250                 255

Cys Val Ser Glu Cys Ile Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Cys Val Ala Ser Asn His Arg Thr Ile Gln Pro Pro Arg Asn Asn
    290                 295                 300

<210> SEQ ID NO 47
<211> LENGTH: 317
<212> TYPE: PRT
<213> ORGANISM: Gallus gallus

<400> SEQUENCE: 47

Met Trp Leu Leu Thr Val Gly Ala Leu Leu Ala Val Leu Gly Ala Gly
1               5                   10                  15

Ser Thr Gln Leu Val Phe Asn Ala Val Asp Phe Val Glu Lys Tyr Ala
                20                  25                  30

Cys Asn Asp Thr Val Val Leu Pro Cys Ile Val Thr Asn Leu Lys Glu
            35                  40                  45

Asn Asn Asp Ser Ser Met His Val Ser Trp Lys Arg Gln Gly Gln Val
        50                  55                  60

Ile Phe Ser Phe Asn Gly Pro Glu Gln Arg Ile Tyr Arg His Glu Ser
65                  70                  75                  80

Val Pro Ser Ala Asn Phe Leu Ser Lys Ala Asp Leu Phe Lys Gly Ile
                85                  90                  95

Ala Ser Leu Arg Leu Lys Asn Ala Glu Ala Pro Asp Gly Asn Tyr Ser
            100                 105                 110

Cys Glu Val Thr Glu Leu Asn Arg Glu Gly Glu Thr Lys Met Lys Leu
        115                 120                 125

Arg Thr His Met Val Asp Ser Cys Asp Glu Glu Lys Pro Pro Thr Pro
    130                 135                 140

Val Asp Lys Cys Glu Arg Gln Phe Asp Phe Ile Gln Ser Ile Val Ile
145                 150                 155                 160

Ala Val Leu Leu Phe Phe Ile Ile Leu Cys Trp Ala Gln Leu Gly
                165                 170                 175

Val Ile Ala Leu Lys Cys Glu Thr Val Arg Lys Lys Arg His Ile
            180                 185                 190

Thr Ile Ala Cys Ser Ile Phe Thr Val Val Ala Ile Ala Val Val
        195                 200                 205

Leu Phe Ile Gln Asp Gly Ser Ile Ser Met Asn Gln Ile Gly Leu Ala
    210                 215                 220

Phe Thr Ile Leu Pro Ala Gly Leu Leu Met Val Leu Gln Tyr Ser Ile
225                 230                 235                 240

Phe Lys Met Val Leu Asp Asp Leu Thr His Lys Gly Tyr Ala Leu Ile
```

```
                245                 250                 255
Gly Phe Gln Val Val Gly Tyr Ile Val Ala Val Val Gly Phe Ala Leu
            260                 265                 270

Ser Val Ser Ala Cys Pro Ser Val Leu Leu Ser Val Val Ile Ala Gly
        275                 280                 285

Leu Val Val Met Ala Val Ala Asp Leu Leu Ala Leu Ala Tyr Val Tyr
    290                 295                 300

Ser Cys Ser Arg Met Lys Asp His Gln Thr Pro Arg Tyr
305                 310                 315

<210> SEQ ID NO 48
<211> LENGTH: 305
<212> TYPE: PRT
<213> ORGANISM: Pan troglodytes

<400> SEQUENCE: 48

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Met Val Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Leu Gln Pro Pro Arg Asn
    290                 295                 300
```

Asn
305

<210> SEQ ID NO 49
<211> LENGTH: 11
<212> TYPE: PRT
<213> ORGANISM: Artificial Sequence
<220> FEATURE:
<223> OTHER INFORMATION: Synthetic- Ph.D.-7 library format
<220> FEATURE:
<221> NAME/KEY: MISC_FEATURE
<222> LOCATION: (1)..(7)
<223> OTHER INFORMATION: Xaa is any amino acid

<400> SEQUENCE: 49

Xaa Xaa Xaa Xaa Xaa Xaa Xaa Gly Gly Gly Ser
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Synthetic- Ph.D.-12 library format
<220> FEATURE:
<221> NAME/KEY: MISC_FEATURE
<222> LOCATION: (1)..(12)
<223> OTHER INFORMATION: Xaa is any amino acid

<400> SEQUENCE: 50

Xaa Xaa Xaa Xaa Xaa Xaa Xaa Xaa Xaa Xaa Xaa Xaa Gly Gly Gly Ser
1               5                   10                  15

<210> SEQ ID NO 51
<211> LENGTH: 14
<212> TYPE: PRT
<213> ORGANISM: Artificial Sequence
<220> FEATURE:
<223> OTHER INFORMATION: Synthetic- Ph.D.-C7C library format
<220> FEATURE:
<221> NAME/KEY: MISC_FEATURE
<222> LOCATION: (3)..(9)
<223> OTHER INFORMATION: Xaa is any amino acid

<400> SEQUENCE: 51

Ala Cys Xaa Xaa Xaa Xaa Xaa Xaa Xaa Cys Gly Gly Gly Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 52

Val Glu Asp Leu Asn Asp Val His His Met Met Thr
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 53

Gly Ile Ser Asp Tyr Ile Gly Gly Lys His His Val
1               5                   10

```
<210> SEQ ID NO 54
<211> LENGTH: 12
<212> TYPE: PRT
<213> ORGANISM: Artificial Sequence
<220> FEATURE:
<223> OTHER INFORMATION: Synthetic- peptide-based antigen mimic

<400> SEQUENCE: 54

Gly Ile Thr Asp Phe Leu Ser Trp Ser Trp Gln Ala
1               5                   10
```

PHAGE-PEPTIDE CONSTRUCTS FOR STIMULATING AN IMMUNE RESPONSE AGAINST CD47

CROSS-REFERENCE TO RELATED APPLICATIONS

The present application claims the benefit of priority under 35 U.S.C. § 119(e) to U.S. Provisional Application No. 62/905,057, filed on Sep. 24, 2019, and to U.S. Provisional Application No. 62/976,113, filed on Feb. 13, 2020, the contents of which are incorporated herein by reference in their entireties.

SEQUENCE LISTING

A Sequence Listing accompanies this application and is submitted as an ASCII text file of the sequence listing named "169996_00466_ST25.txt" which is 43.2 KB in size and was created on Sep. 24, 2020. The sequence listing is electronically submitted via EFS-Web with the application and is incorporated herein by reference in its entirety.

BACKGROUND

The present subject matter relates to the field of recombinant bacteriophage constructs that express exogenous peptide sequences for inducing immune responses. In particular, the present subject matter relates to recombinant phage constructs that express exogenous peptide sequences and bind to anti-CD47 antibodies. The recombinant phage constructs and the expressed exogenous sequence can be administered to a subject in need thereof in order to generate an immune response against CD47 in the subject, including generating anti-CD47 antibodies.

CD47 is a cell surface protein that belongs to the immunoglobulin superfamily. CD47 binds several proteins including signal-regulatory protein-alpha (SIRPα) expressed on phagocytes. Binding of CD47 to SIRPPα leads to inhibition of phagocytosis. In this respect, CD47 plays a role of a "don't eat me" signal for phagocytic cells, making cells expressing CD47 resistant to phagocytosis. CD47 is widely expressed at low levels on a majority of normal cells. CD47 also is found on many tumors, but at much higher levels which shields cancer cells from destruction by the immune cells. One way to disarm the "don't eat me" signal on cancer cells is to block CD47 with molecules that prevent the CD47-SIRPα interaction such as neutralizing monoclonal antibodies (mAb) against CD47. This approach was demonstrated to be effective in many hematologic and solid malignancies, including non-Hodgkin lymphoma, acute lymphocytic leukemia, multiple myeloma, brain, breast, ovarian, colon, bladder, pancreatic, and small cell lung cancer (reviewed in Weiskopf, 2017, European J Cancer, 76,100-109). Several of the studies demonstrated that CD-47 mAb not only inhibited the growth of primary tumors, but also prevented formation of tumor metastases in lymph nodes and lungs. Importantly, although CD47 is expressed on both cancer and normal cells, antibodies blocking CD47 selectively target cancer, but not normal cells. A plausible explanation for such selectivity is that healthy normal cells lack a secondary pro-phagocytic "eat me" signal, and, in the absence of CD47-SIRPα signaling, are not subject to phagocytic activity of macrophages (Willingham et al., 2012, Proc Natl Acad Sci USA, 109, 6662-67). Human clinical trials for solid and hematologic malignancies using CD47 mAbs are in progress showing that the therapy is well tolerated. Remarkably, CD47 was also identified as an important anti-cancer target for treatment of canine lymphoma (Weiskopf et al., 2016, Cancer Immunol Res, 1072-1087), one of the most common types of canine cancer, demonstrating the utility of CD47-based therapies in veterinary patients.

Passive immunotherapies with mAbs have become the standard of care for many human diseases, including cancer. The list of therapeutic mAbs on the market included 47 products in 2014 and continues to grow at the rate of ~4 new products per year. Combined world-wide sales of mAb products are expected to be nearly $125 billion in 2020 (Ecker et al., 2015, mAbs, 7, 9-14). The downside of monoclonal antibody therapy is its very high cost that can be hundreds of thousands of dollars per treatment course (Science, 2013, 342:1432-1433). For example, cost of a breast cancer drug Herceptin, probably the least expensive anti-cancer mAbs drug on the market, is around $70,000 for a one-year course of treatment. It is obvious that such costs are absolutely prohibitive for millions of people without medical insurance. Not all insurances can cover such expenses either. Moreover, the cost of mAb-based therapies is not just prohibitive for many individuals, but also might be unsustainable for the society (Health Economics, 2015, 8:9).

Active immunotherapies against cancer, in contrast, can be both, effective and affordable, since active immunization does not require infusion of multiple doses of extremely expensive anti-cancer antibodies, but rather stimulates the body to produce its own antibodies. One example of active anti-cancer therapy reported in the literature is anti-GD2 immunotherapy for neuroblastoma (Expert Rev Anticancer Ther., 2017, 17(10):889-904). Another example is poxvirus-based cancer vaccine CV301 designed to target carcinoembryonic antigen (CEA) and mucin1 protein (MUC1), two tumor-associated antigens that are over-expressed in multiple solid tumors, including lung, bladder, colorectal, and pancreatic cancers (Clin Cancer Res, 2011, 17:7164-7173; Expert Rev Anticancer Ther, 2017, 17(10):889-904).

Therefore, there is a need for active immunotherapies against CD47. Here, the inventors describe recombinant phage that express exogenous peptides which can be utilized to actively stimulate production of blocking CD47 antibodies.

SUMMARY

Disclosed are recombinant bacteriophage constructs that express exogenous peptide sequences for generating immune responses against CD47, otherwise referred to as integrin associated protein (IAP). The disclosed recombinant phage constructs express exogenous peptide sequences and bind to antibodies against (CD47). The disclosed recombinant phage constructs and exogenous peptide sequences and can be administered to a subject in need thereof in order to generate an immune response against CD47, including generating anti-CD47 antibodies. The exogenous peptide sequence of the disclosed recombinant phage may comprise an amino acid sequence of CD47, epitopic fragments, variants, or functional mimics thereof.

Also disclosed are methods for making and selecting such recombinant phage constructs and exogenous peptides, and compositions that comprise such constructs and exogenous peptides (e.g., compositions for inducing an immune response against CD47 including pharmaceutical or veterinary compositions used as vaccines). Also disclosed are recombinant polynucleotides encoding the recombinant phage constructs and peptides disclosed herein, as well as expression vectors for expressing the disclosed peptides.

The exogenous peptide of the disclosed recombinant phage constructs typically includes one or more epitopes of CD47 or functional mimics thereof. The exogenous peptide may be at least 5, 6, 7, 8, 9, or 10 amino acids in length.

The exogenous peptide of the disclosed recombinant phage constructs may include an amino acid sequence of CD47 (e.g., SEQ ID NO:42 (human) or SEQ ID NO:43 (dog)), epitopic fragments, variants, or functional mimics thereof. In some embodiments, the exogenous peptide comprises, consists essentially of, and/or comprises an amino acid sequence selected from GLSDYYRALAN (SEQ ID NO:1), GITEYLRTINIG (SEQ ID NO: 2), DYSLRLQYGHTY (SEQ ID NO:3), GLTDYLG (SEQ ID NO:4), EYVAPFNFLEWK (SEQ ID NO:5), YSDTSLSYMQRY (SEQ ID NO:6), AND GLGDRLSHGHTI (SEQ ID NO:7).

The exogenous peptide may comprise an amino acid sequence having a percentage of sequence identity to any of the peptides disclosed herein (e.g., any of SEQ ID NOS:1-43). For, example, the exogenous peptide may comprise an amino acid sequence having at least about 20%, 30%, 40%, 50%, 60%, 70%, 80%, or 90% sequence identity to any of SEQ ID NOS:1-43.

The exogenous peptide may be inserted within and/or fused to a protein of the bacteriophage. For example, the exogenous peptide may be inserted within a gpIII or gpVIII protein of the bacteriophage.

Also disclosed are immunogenic compositions that include the disclosed recombinant phage constructs and/or the exogenous peptides, and a suitable excipient, carrier or diluent. The compositions further may comprise an adjuvant. The compositions may be formulated as pharmaceutical or veterinary compositions, for example, for administering as a vaccine.

The immunogenic compositions may be administered to subjects in need thereof in methods for generating an immune response against CD47, which may include B-cell responses (e.g., antibody responses against CD47) and/or T-cell responses. The immunogenic compositions may be administered to a subject in methods for treating cancers that express CD47.

BRIEF DESCRIPTION OF THE FIGURES

FIG. 11. Table summary of the performance of the p3-targeted workflow.

DETAILED DESCRIPTION

Figure 1:
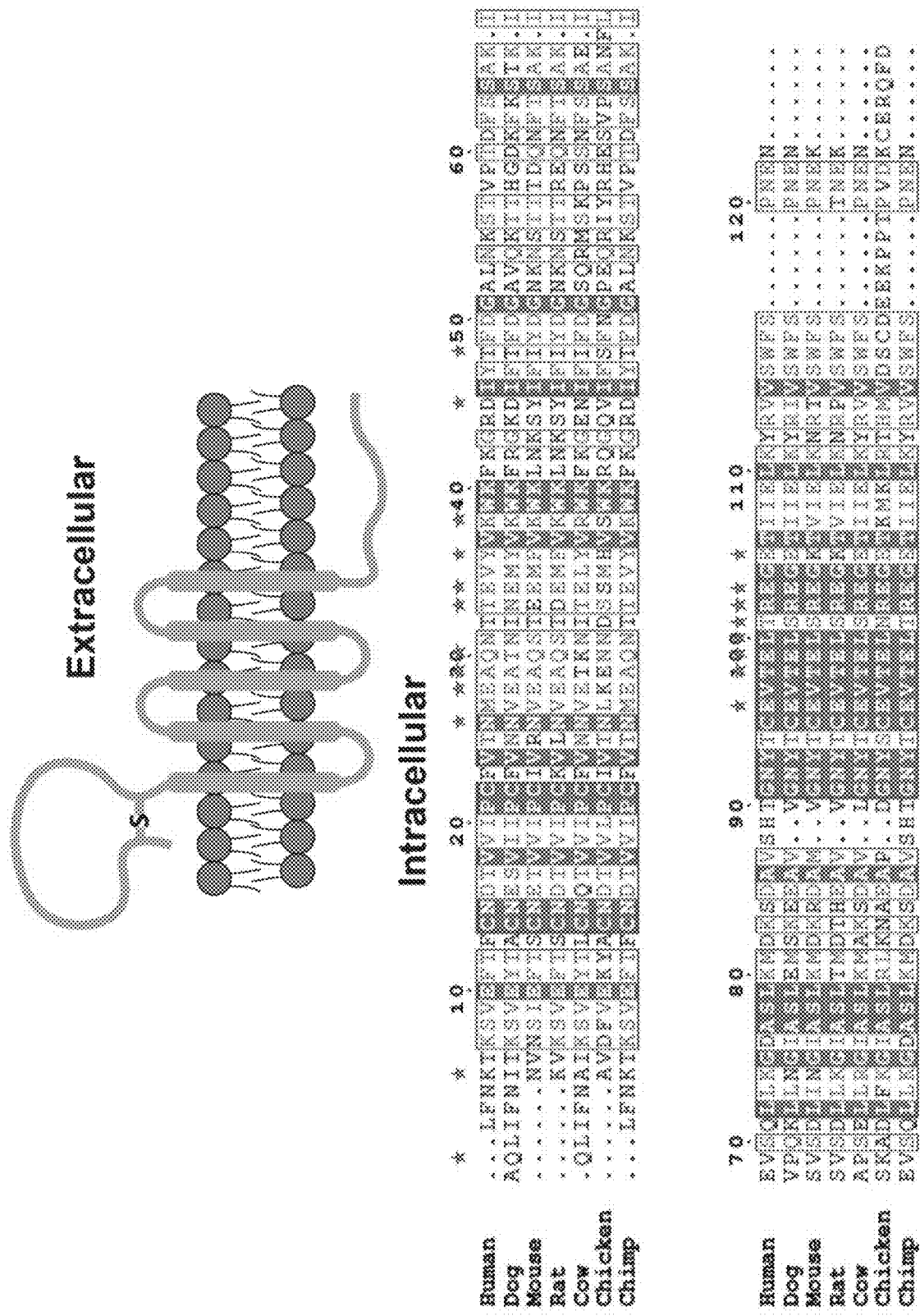
FIG. 1. Schematic structure of CD47 including extracellular domain, transmembrane domains, and intracellular domain. Sequence alignment of CD47 from human (SEQ ID NO:42), dog (SEQ ID NO:43), mouse (SEQ ID NO:44), rat (SEQ ID NO:45), cow (SEQ ID NO:46), chicken (SEQ ID NO:47), and chimp (SEQ ID NO:48) demonstrating sequence homology and conservation.

The disclosed subject matter may be further described using definitions and terminology as follows. The definitions and terminology used herein are for the purpose of describing particular embodiments only, and are not intended to be limiting.

Unless otherwise specified or indicated by context, the terms "a", "an", and "the" mean "one or more." For example, "a peptide" should be interpreted to mean "one or more peptides" unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

The recombinant phage and exogenous peptides disclosed herein bind specifically to anti-CD47 antibodies. Furthermore, the recombinant phage and exogenous peptides disclosed herein contemplated herein may be utilized in immunogenic compositions or vaccines for eliciting antibodies that bind specifically to CD47. In this regard, the terms "binds specifically" and "bind specifically" refer to that interaction between the recombinant phage and exogenous peptides and anti-CD47 antibodies. The interaction is dependent upon the presence of a particular structure of the recombinant phage or exogenous peptides, e.g., the antigenic determinant or epitope present on the recombinant phage or exogenous peptides, recognized by the anti-CD47 antibody or binding molecule. For example, if the anti-CD47 antibody is specific for epitope "A," the presence of a recombinant phage or exogenous peptides comprising the epitope A, or the presence of free unlabeled A, in a reaction containing free labeled A and the anti-CD47 antibody will reduce the amount of labeled A that binds to the anti-CD47 antibody.

Peptides, Polypeptides, Proteins, and Synthesis Methods

In some aspects, the disclosed subject matter relates to proteins, polypeptides, and/or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine residues. The term "amino acid residue" may include alpha-, beta-, gamma-, and delta-amino acids.

In some embodiments, the term "amino acid residue" may include nonstandard, noncanonical, or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard, noncanonical, or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenyl-alanine, a p-amino-L-phenylalanine, an isopropyl-L-phenyl-alanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, ufahor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α, α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions. The disclosed recombinant bacteriophage may include an insertion in the form of an exogenous peptide sequence inserted within or fused to a native protein of the bacteriophage.

Regarding proteins, polypeptide, and peptides, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, polypeptides, and peptides, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Gln, His |
| Glu | Asp, Gln, His |
| Gly | Ala |
| His | Asu, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The disclosed proteins, polypeptides, peptides, mutants, variants, as described herein may have one or more functional or biological activities exhibited by a reference polypeptide (e.g., one or more functional or biological activities exhibited by wild-type protein).

Preferably, the recombinant phage and exogenous peptides disclosed herein selectively bind to anti-CD47 antibodies relative to control antibodies (e.g., preimmune serum). The recombinant phage and exogenous peptides disclosed herein may exhibit at least two-fold, three-fold, four-fold, five-fold, six-fold, seven-fold, ten-fold, twenty-fold, thirty-fold or more increased binding affinity for anti-CD47 antibodies relative to control antibodies. Recombinant phage and exogenous peptides that exhibit such binding characteristics are said to exhibit preferential binding to anti-CD47 antibodies. Recombinant phage and exogenous peptides that do not exhibit at least a two-fold increased binding affinity for anti-CD47 antibodies relative to control antibodies are simply said to bind to anti-CD47 antibodies.

The disclosed proteins, polypeptides, and peptides may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

A composition as disclosed herein my comprise the proteins, polypeptides, and peptides, wherein the proteins, polypeptides, and peptides represent at least about 50%, 60%, 70%, 80%, 90%, 95%, 96%, 97%, 98% or 99% of all proteins, polypeptides, and peptides in the composition.

A composition may be substantially homogenous in regard to the composition's content of proteins, polypeptides, and peptides as discloses herein. For example, a composition may comprise a protein, polypeptide, or peptide and may not comprise any other protein, polypeptide, or peptide.

A homogenous population of bacteriophage refers to a population of bacteriophage in which each bacteriophage is substantially identical. For example, a homogenous population of bacteriophage may be defined as a population that comprises a bacteriophage that expresses an exogenous peptide wherein the population does not comprise a bacteriophage that expresses another different exogenous peptide (e.g., wherein each phage of the homogenous population of phage comprises the same exogenous peptide).

The proteins, polypeptides, and peptides disclosed herein may be expressed from a "translation template." As used herein, "translation template" refers to an RNA product of transcription from an expression template that can be used by ribosomes to synthesize polypeptides or proteins.

The proteins, polypeptides, and peptides disclosed herein may be expressed in culture. For example, the proteins, polypeptides, and peptides disclosed herein may be expressed in bacteriophage culture The proteins, polypeptides, and peptides disclosed herein may be expressed in a "reaction mixture." The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The peptides disclosed herein may be fused or conjugated to one or more other peptides or non-peptide moieties (e.g., in order to provide an antigen). For example, a fusion polypeptide as contemplated herein may include a fusion of any of the peptides or motifs of SEQ ID NO: 1-43 and one or more other peptides. The peptides disclosed herein may be present in a polypeptide (e.g., where the polypeptide comprises one or more copies of the amino acid sequence of the peptide, optionally in tandem). The disclosed peptides may be modified to enhance immunogenicity. For example, the peptides disclosed herein may be conjugated to one or more carrier proteins. Suitable carriers may include but are not limited to *Haemophilus influenzae* protein D (PD), *Neisseria meningitidis* porin protein (PorA), *Corynebacterium diphtheriae* toxin (CRM197), and *Clostridium tetani* toxin (TT).

Polynucleotides and Synthesis Methods

In some aspects, the disclosed subject matter related to polynucleotides. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms "nucleic acid" and "oligonucleotide," as used herein, refer to polydeoxyribonucleotides (containing 2-de-oxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Figure 13:
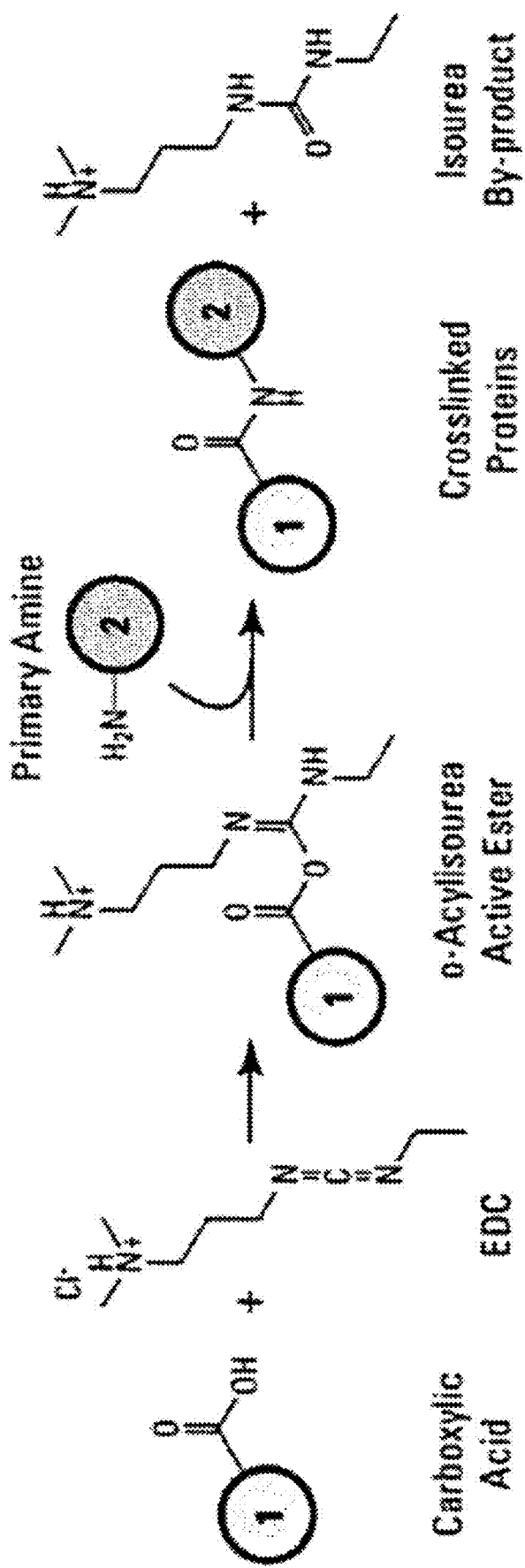
FIG. 13 shows an exemplary synthesis of crosslinked proteins of the present invention.
Figure 14:
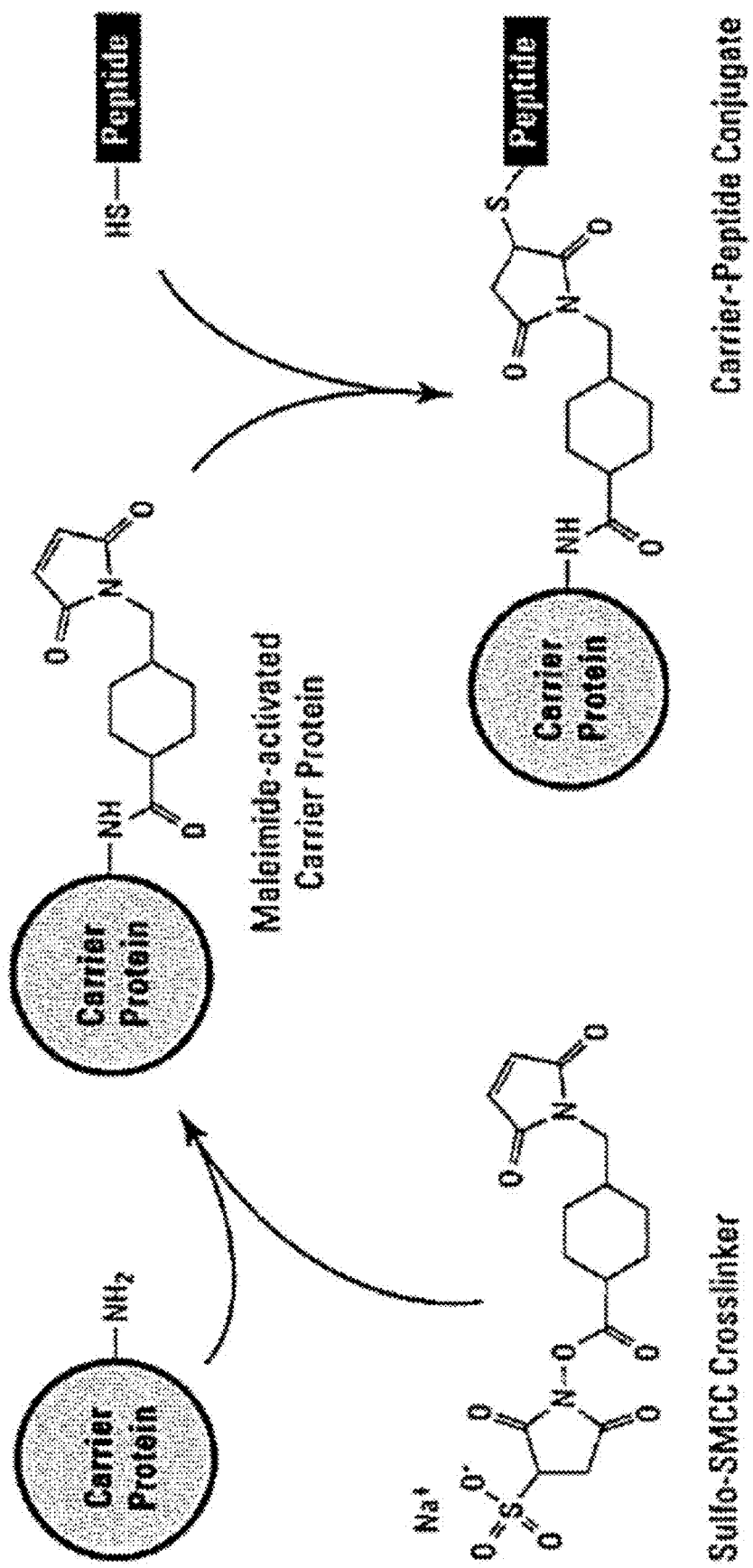
FIG. 14 shows an exemplary method for synthesizing a carrier-peptide conjugate.
Figure 15:
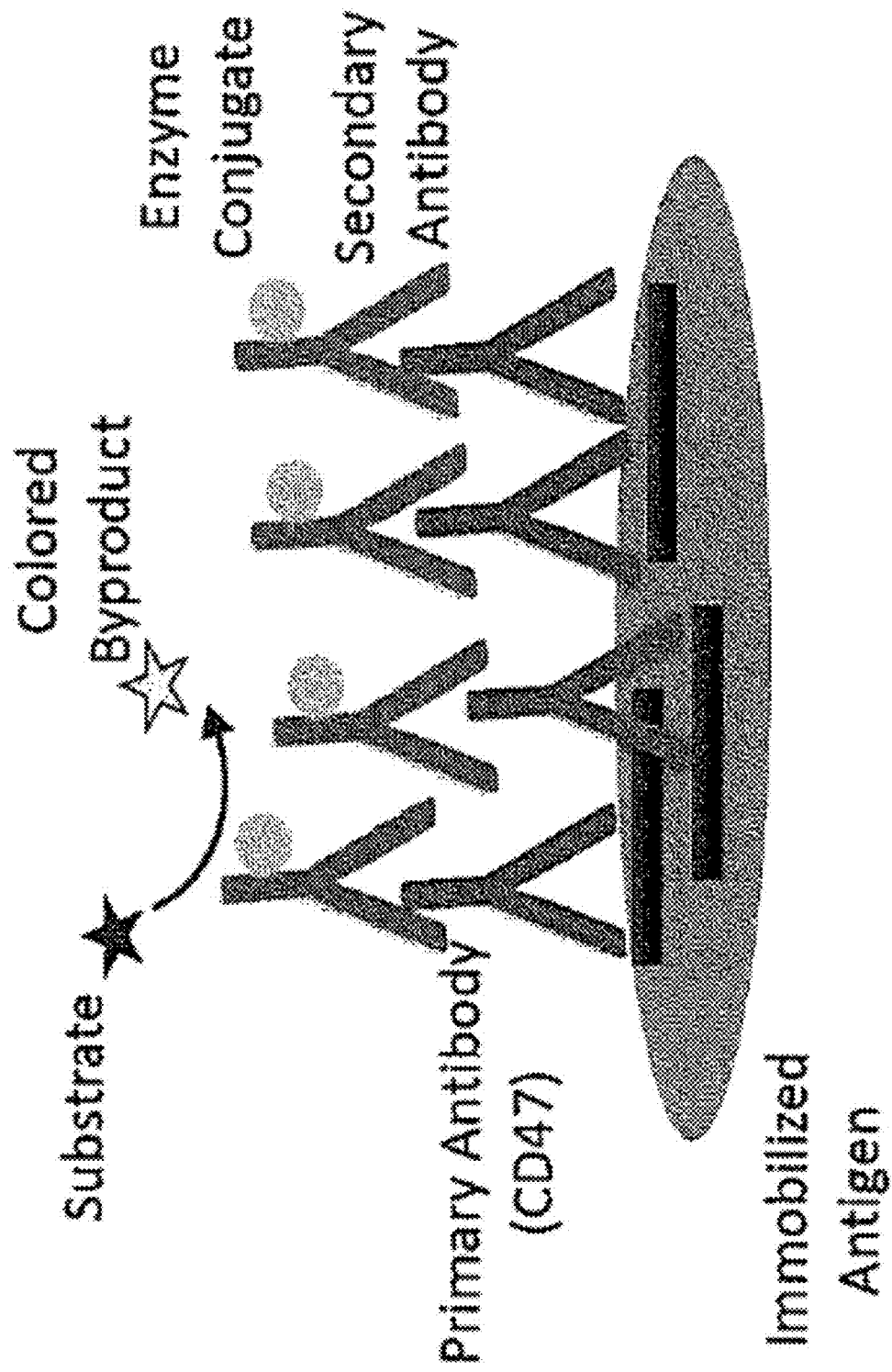
FIG. 15 shows an exemplary method for analyzing phage-peptide constructs using a CD47 indirect ELISA versus unmodified phages.
Figure 16:
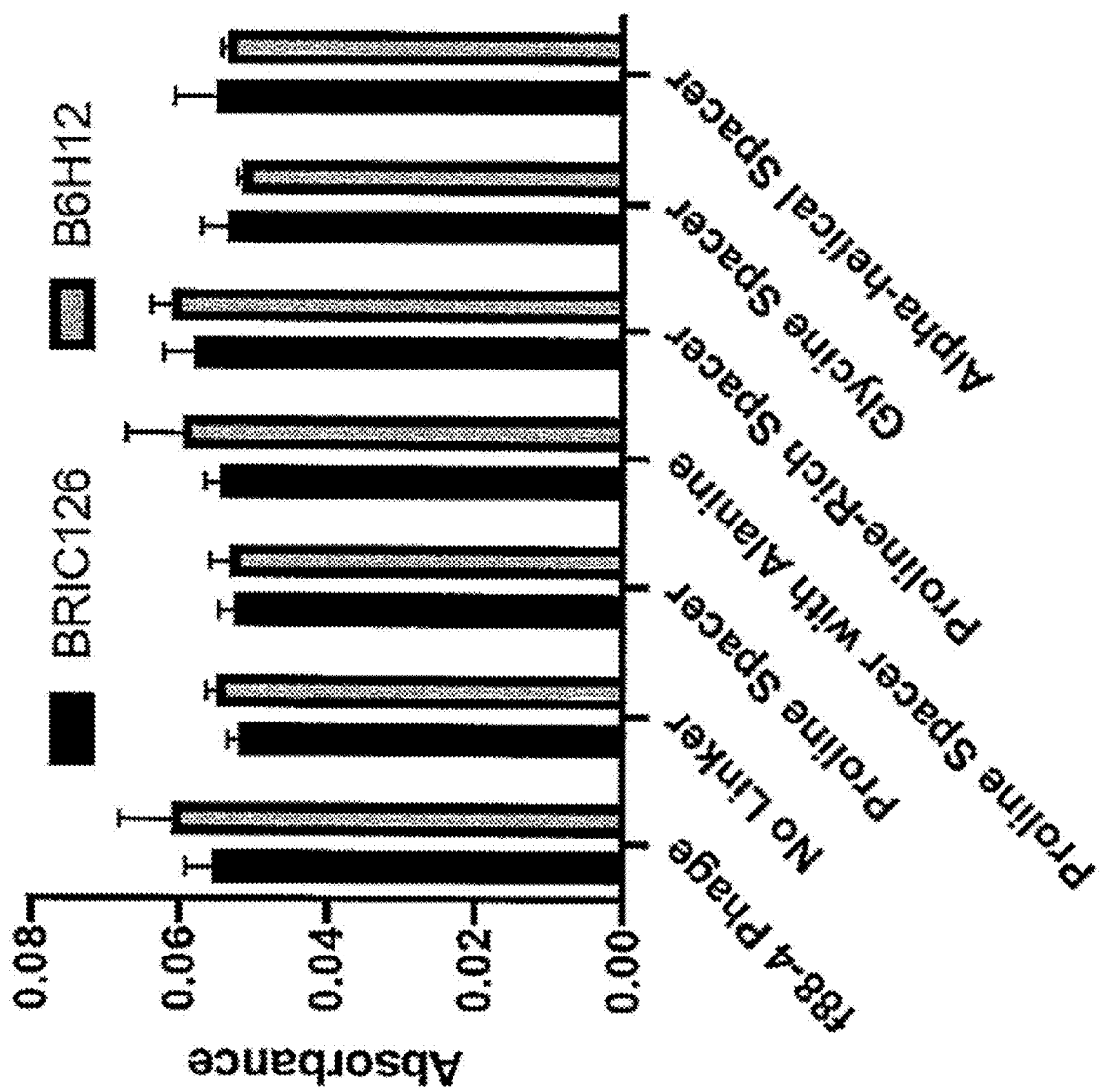
FIG. 16 shows binding of CD47 antibody to genetic constructs of the instant disclosure by indirect ELISA.
Figure 17:
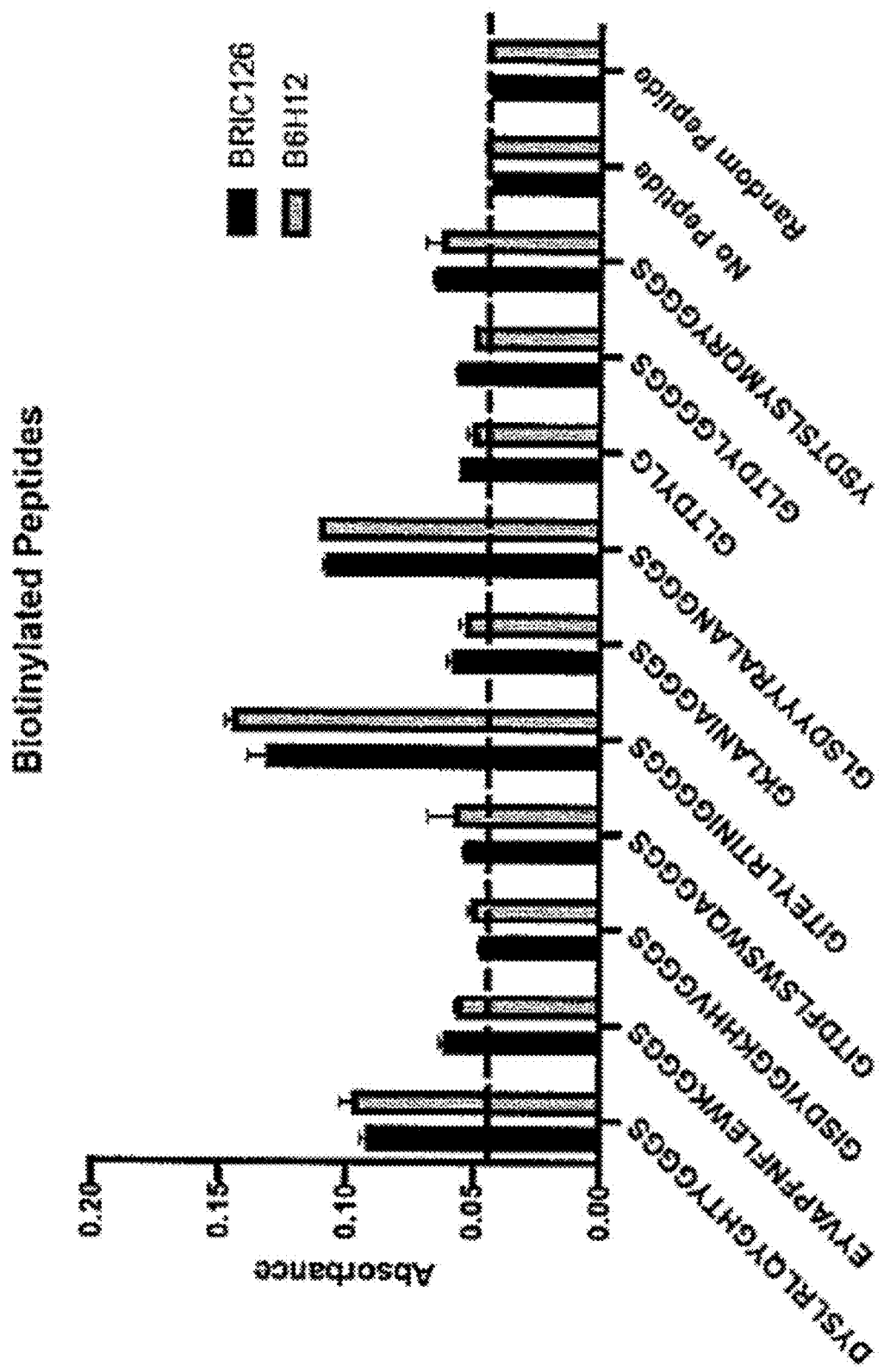
FIG. 17 shows results of indirect anti-CD47 antibody ELISA with the indicated targets. From right to left the peptides have the sequence identifiers SEQ ID NOs: 8, 9, 10, 11, 12, 13, 14, 4, 15, and 16.
Figure 18:
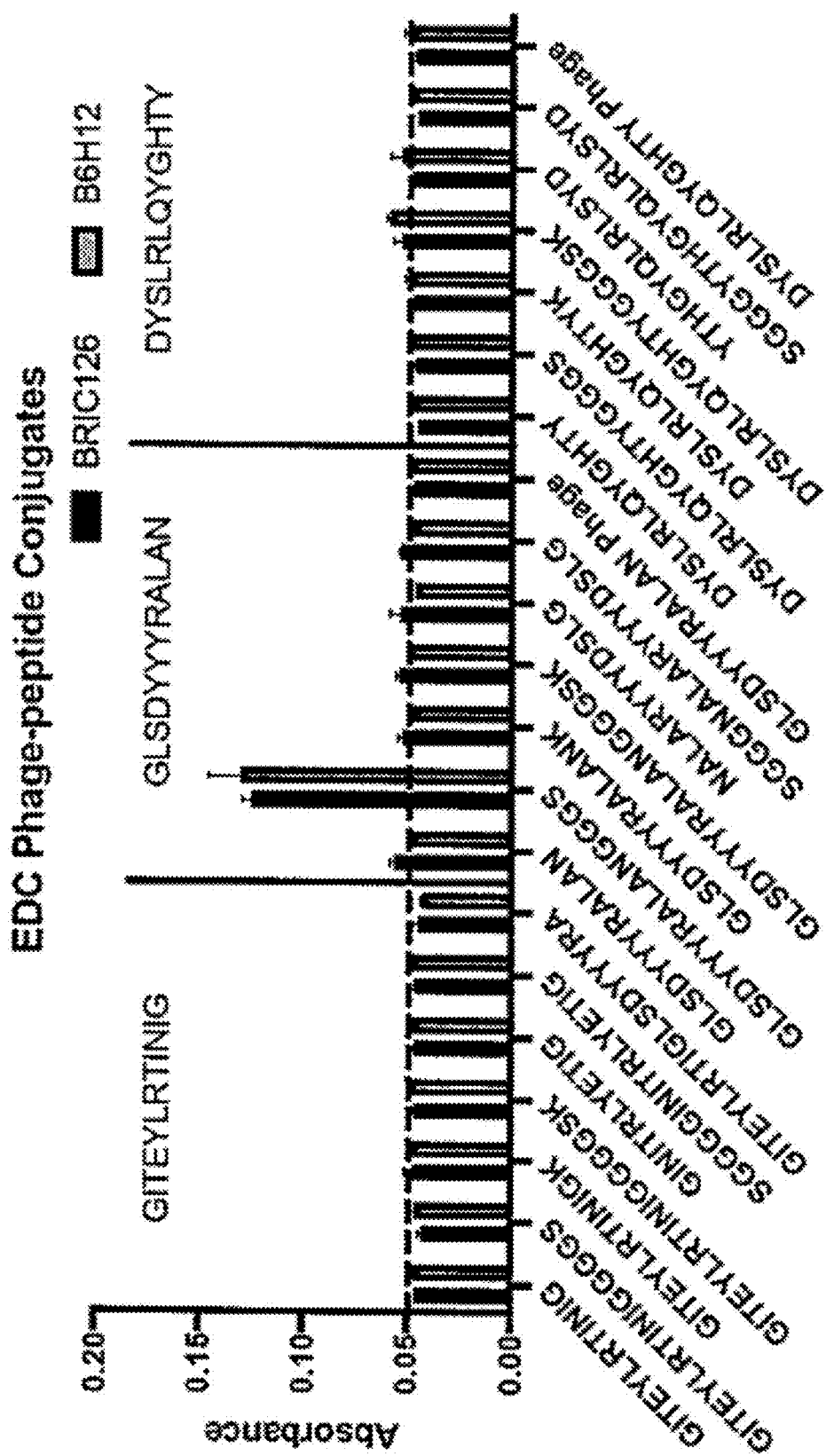
FIG. 18 shows results of indirect anti-CD47 antibody ELISA with the indicated targets. From right to left the peptides have the sequence identifiers SEQ ID NOs: 2, 17, 18, 19, 20, 21, 22, 23, 24, 25, 26, 27, 28, 23, 3, 29, 30, 31, 32, 33, and 3.
Figure 19:
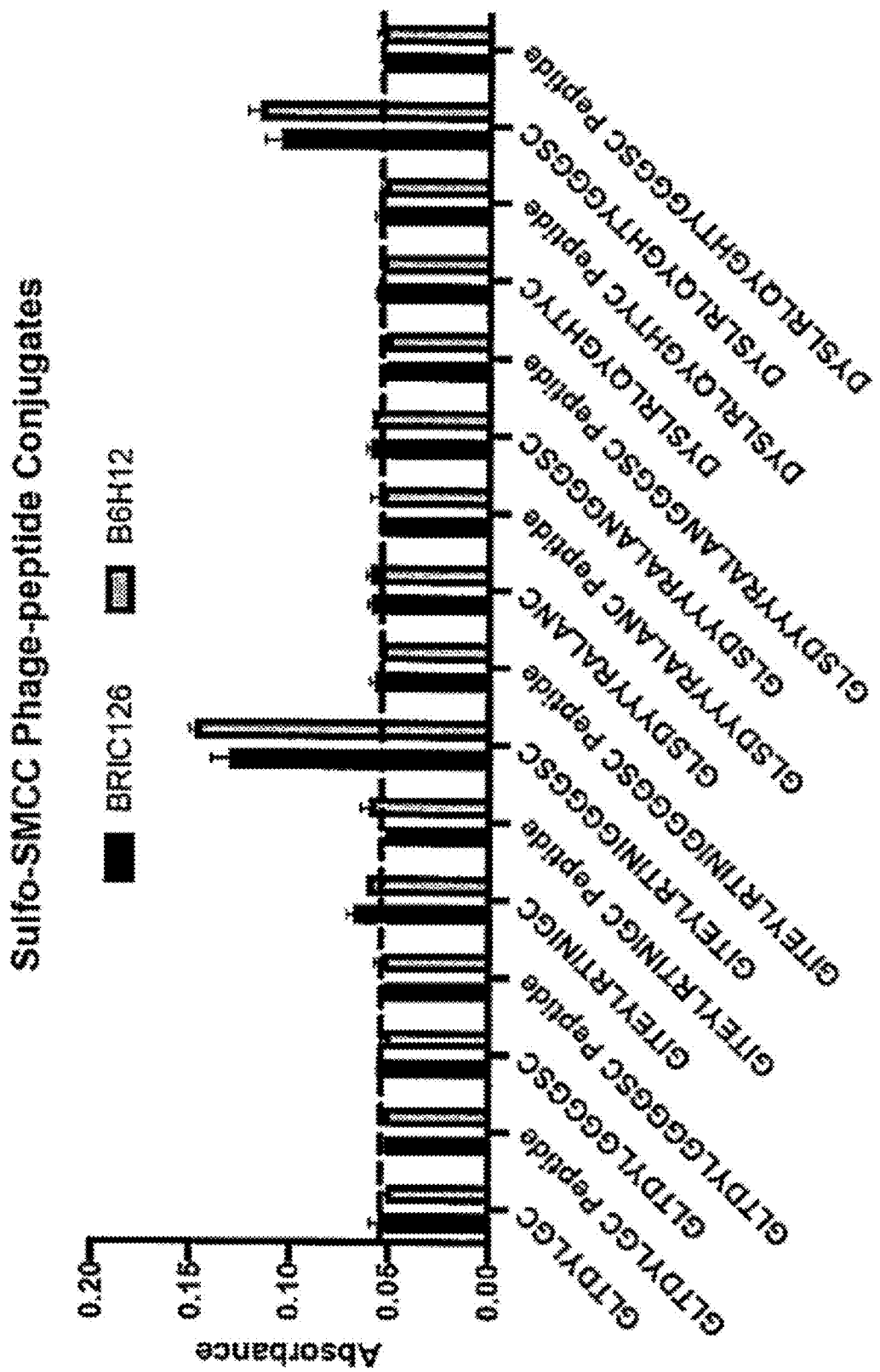
FIG. 19 shows results of indirect anti-CD47 antibody ELISA with the indicated targets. From right to left the peptides have the sequence identifiers SEQ ID NOs: 34, 34, 35, 36, 37, 37, 38, 38, 39, 39, 40, 40, 41, and 41.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized and/or codon-adapted for expression in a particular host. In the art, codon usage frequency tables have been prepared for a number of host organisms including humans, mouse, rat, pig, *E. coli*, plants, and other host cells. In some embodiments, the polynucleotide sequences disclosed herein may encode a protein (e.g., a reporter protein such as luciferase) and may be codon-optimized and/or codon-adapted for expression in Clostridia (e.g., *Clostridium acetobutylicum*, *Clostridium autoethanogenum* and/or *E. coli* (see, e.g., SEQ ID NOs: 17-20 and FIG. 13).

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g. T3 RNA polymerase, T7 RNA polymerase, SP6 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more proteins, polypeptides, peptides and/or recombinant phage described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions. A "mammalian expression vector," is an expression vector that has been designed to express an encoded protein in mammalian cells.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

The exogenous peptides disclosed herein may be expressed via vectors that include viral, bacterial, or other vectors. In some embodiments, the exogenous peptides are expressed via a recombinant filamentous bacteriophage (i.e., Ff class bacteriophages). Bacteriophages (or phages) are viruses that infect bacteria. They consist of an outer protein capsid enclosing genetic material (single stranded circular DNA). Filamentous phages (Ff class) are long (~1 μm) and thin (~7 nm) particles. Such particles can be genetically re-engineered and utilized as carriers for immunogenic peptides, which are displayed on phage surfaces as fusion molecules to phage coat proteins. (See Minenkova et al., Gen. 1993:85-88; and Yip et al., Immunol. Lett. 2001 Dec. 3; 79(3):197-202). To create fusion peptides, a foreign oligonucleotide usually is inserted into the phage minor coat protein gene 3 or the phage major coat protein gene 8. Inserts in gene 3 produce fusions with a maximum of 5 copies of protein (gpIII). Inserts in gene 8 produce multiple fusion peptides, the number of which depends on the phage vector design. Usually, protein (gpVIII) vectors contain two copies of gene 8, one of which encodes the wild-type protein, and the other encodes a fusion protein. Such vector design results in irregular phage surface architecture that contains a variable number (from 15 to 300) of fusion peptides separated by wild-type phage proteins. However, by using a bacteriophage vector that has only one copy of gene 8, all copies of the major coat protein VIII are modified with the fusion peptide. (See Petrenko et al., Protein Eng. 1996 September; 9(9):797-801). Such a bacteriophage may otherwise be referred to as a "landscape phage" in view of the dramatic change in surface structure of the phage caused by the >1000 copies of the exogenous peptide present in a dense, repeating pattern on the phage's tubular capsid. In landscape phage, foreign peptides are expressed in each copy of the phage major coat protein VIII, resulting in a surface density of as many as 4000 foreign peptide copies per phage particle. Most importantly, high density epitopes in the landscape phage are presented in a highly-organized manner and are properly spaced for binding to B cell receptors. Such repetitive highly-organized epitope patterns usually permit a cross-linking activation of B-cell receptors, which provides robust, long-lasting immune responses. (See Bachmann et al., Annu. Rev. Immunol. 1997; 15:235-70; and Fehr et al., Proc. Natl. Acad. Sci. USA 1998 Aug. 4; 95(16):9477-81). Additionally, phage are able to stimulate strong T helper cell responses. (See Gaubin et al., DNA Cell Biol. 2003 January; 22(1):11-18; Hashemi et al., J. Virol. Methods 2010 February; 163(2):440-444; Ulivieri et al., Immunol. Lett. 2008 Aug. 15; 119(1-2):62-70; and Wan et al., Eur. J. Immunol. 2005 July; 35(7:2041-50). Phage particulate nature, size and shape further appeal for its strong/long-lasting immunogenic potentials. Filamentous phage has been shown to naturally stimulate both B and T helper cell responses without adjuvants. (See De Berardinis et al., Expert Rev. Vaccines 2004 December; 3(6):673-9; and Manoutcharian et al., Curr. Pharm. Biotechnol. 2001 September; 2(3):217-23). Although they can not infect animal cells, landscape phage may be inactivated prior to subsequent use in an immunogenic or vaccine composition.

Phages, as bacterial viruses, can be easily obtained in large quantities from bacterial cultures, which makes the cost of phage preparations much lower than the cost of peptides vectored in mammalian viruses or the cost of production of synthetic peptides. Importantly, landscape phage preparations are very thermostable. They resist degradation and retain antigenicity for more than six months at room temperature, more than six weeks at 63° C., and three days at 76° C. (see Brigati et al., Anal. Bioanal. Chem. 2005 July; 282(6):1346-50), making landscape phage-based preparations ideally suited for shipping, storage, and delivery in field conditions without requiring refrigeration. Examples of phage-based (non-landscape phage) vaccines reported in the literature include preparations for treatment of melanoma (Eriksson et al., Cancer Immunol. Immunother. 2007 May; 56(5):677-87; and Eriksson et al., J. Immunol. 2009 Mar. 1; 182(5):3105-11), HIV (see De Berardinis et al., Curr. HIV Res. 2003 October; 1(4):441-6), Alzheimer's disease (see Frenkel et al. Vaccine 2003 Mar. 7; 21(11-12):1060-5), candidiasis (see Wang et al., Vaccine 2006 Aug. 28; 24(35-36):6065-73; and Yang et al., Mycoses 2007 May; 50(3):165-71), and rabies (see Houimel et al., Vaccine 2009 Jul. 23; 27(34):4648-55). Filamentous phage preparations based on fd phage (same as landscape phage) have been used experimentally in humans with the approval of the FDA and with no apparent side effects (see Krag et al., Cancer Res. 2006 Aug. 1; 66(15):7724-33), indicating their safety.

Recombinant phage particles displaying fusion peptides can be obtained via cloning of oligonucleotides encoding for the fusion peptides in phage display vectors. Alternatively, phage clones displaying desired peptides or their structural/functional mimics can be selected from phage display libraries.

The presently disclosed peptides, polypeptides, landscape phage, or vectors may be isolated or substantially purified. The terms "isolated" or "substantially purified" refers to peptides, polypeptides, landscape phage, or vectors that have been removed from their environment and have been isolated or separated, and are at least 60% free, preferably at least 75% free, and more preferably at least 90% free, and most preferably at least 95%, 96%, 97%, 98%, or 99% free from other components with which they were naturally associated (such as other bacteriophage in the example of a homogenous population of bacteriophage as contrasted with a bacteriophage library).

Methods of Use

In some aspects, the disclosed methods related to methods for inducing an immune response against CD47. In some embodiments, the methods include inducing polyclonal antibodies against CD47 by administering to a subject in need thereof an immunogenic composition that includes a recombinant phage comprising an exogenous peptide or the exogenous peptide itself free from the recombinant phage. The subject may be a human or non-human animal (e.g., a non-human mammal). The induced polyclonal antibodies may include anti-CD47 antibodies. The methods disclosed herein also may include treating cancer characterized by expression of CD47 in a subject in need thereof by administering to the animal an immunogenic composition that includes recombinant phage comprising an exogenous peptide or the exogenous peptide itself free from the recombinant phage. For example, a subject having cancer characterized by expression of CD47 may be treated by administering to the subject a composition that includes a recombinant phage comprising an exogenous peptide or the exogenous peptide itself free from the recombinant phage together with a suitable excipient.

The disclosed compositions may be formulated and administered as immunogenic compositions or vaccines utilizing a selected "prime-boost vaccination regimen." As used herein, a "prime-boost vaccination regimen" refers to a regimen in which a subject is administered a first composition one or more times (e.g., one time or two or three times with about 2, 3, or 4 weeks between administrations) and then after a determined period of time after having administered the first composition (e.g., about 2 weeks, about 4 weeks, about 2 months, about 3 months, about 4 months, about 5 months, about 6 months, or longer), the subject is administered a second composition which may be the same or different ast the first composition. In some embodiments, the second composition may also be administered more than once, with at least 2, 3, or 4 weeks between administrations.

Also disclosed are immunogenic compositions and vaccines for performing the disclosed methods. The immunogenic or vaccine compositions may comprise a recombinant phage comprising an exogenous peptide as disclosed herein, another vector that expresses the disclosed exogenous peptides, or the exogenous peptides themselves. The disclosed immunogenic or vaccine compositions may be monovalent or polyvalent. For example, the immunogenic compositions may include one or more landscape phage that express one or more different exogenous peptides, one or more other vectors that express the disclosed exogenous peptides, or one or more of the exogenous peptides themselves. The immunogenic compositions also may include a suitable excipient, carrier, or diluent.

Suitable peptides for the immunogenic compositions (or for expression by vectors of the immunogenic compositions) may include one or more peptides as disclosed herein (e.g., one or more peptides of SEQ ID NOS:1-43). In some embodiments, the immunogenic compositions may include two or more peptides (or two or more vectors that express two or more peptides) where each peptide comprises the amino acid sequence of any of SEQ ID NOS:1-43. The immunogenic compositions may include an isolated peptide at a concentration sufficient to induce an immunogenic response against CD47 (e.g., via antibody induction, a T-cell response, or both), or the immunogenic compositions may include one or more vectors that express the polypeptide or peptide at a concentration sufficient to induce an immunogenic response against CD47 (e.g., via antibody induction, a T-cell response, or both).

The "immunogenic compositions" and "vaccines" disclosed herein are capable of stimulating an immune response in an animal inoculated with the immunogenic composition or vaccine. An immune response may include induction of antibodies, induction of a T-cell response, or both.

An "an immunogenic composition comprising a given peptide or polypeptide" refers to a composition containing the given peptide or polypeptide. The composition may comprise a dry formulation or an aqueous solution. An "immunogenic peptide or polypeptide" is an antigen which is capable of eliciting an immune response when introduced into a subject in need thereof.

The methods disclosed herein may include administering an immunogenic composition or a vaccine to a human or non-human animal. An "animal," as used herein, may include a non-human mammal.

In some embodiments of the disclosed immunogenic compositions or vaccines, the disclosed peptides may be expressed by a vector other than a landscape phage, for example, eukaryotic expression vectors or bacterial vectors. As used herein, an "eukaryotic expression vector" refers to recombinant nucleic acid that has been engineered to express an exogenous polypeptide in eukaryotic cells (e.g., human or non-human animal cells). Suitable eukaryotic vectors for expressing the peptides disclosed herein may include viral vectores, but are not limited to adenovirus vectors, Sendai virus vectors, and measles virus vectors. Recombinant attenuated bacteria also may be utilized as vectors in the pharmaceutical compositions and vaccines disclosed herein (e.g., recombinant attenuated *Shigella, Salmonella, Listeria*, or *Yersinia*). Recombinant bacterial vaccine vectors are described in Daudel et al., "Use of attenuated bacteria as delivery vectors for DNA vaccines," Expert Review of Vaccines, Volume 6, Number 1, February 2007, pp. 97-110(14); Shata et al., "Recent advances with recombinant bacterial vaccine vectors," Molec. Med. Today (2000), Volume 6, Issue 2, 1 Feb. 2000, pages 66-71; Clare & Dougan, "Live Recombinant Bacterial Vaccines," Novel Vaccination Strategies, Apr. 16, 2004 (Editor Stefan H. E. Kaufman); Gentschev et al., "Recombinant Attenuated Bacteria for the Delivery of Subunit Vaccines," Vaccine, Volume 19, Issues 17-19, 21 Mar. 2001, Pages 2621-2628; Garmory et al., "The use of live attenuated bacteria as a delivery system for exogenous antigens," J. Drug Target. 2003; 11(8-10):471-9; U.S. Pat. Nos. 6,383,496, 6,923,958 (which all are incorporated by reference herein in their entireties). Preferably, the vector is species-specific, whereby the vector selectively infects a target species of animal or the vector selectively expresses an encoded exogenous peptide in the target species of animal after infecting the animal.

The immunogenic compositions or vaccines may be formulated for delivery in any suitable manner. For example, the immunogenic compositions or vaccines may be formulated for at least one of oral delivery, intranasal delivery, intramuscular delivery, subdermal delivery, subcutaneous delivery, intravenous delivery, and intraperitoneal delivery. The immunogenic compositions or vaccines can be administered using a variety of methods including intranasal and/or parenteral (e.g., intramuscular) administration. In some embodiments of the methods, the immunogenic composition or vaccine is administered intramuscularly one or more times at suitable intervals (e.g., at intervals of 2-4 weeks), followed by administration of the immunogenic composition or vaccine at least once intramuscularly or intranasally after a suitable time period (e.g., 2-4 weeks after the last parenteral administration of vaccine). The immunogenic compositions or vaccines may be administered to an animal of either sex. In some embodiments, the animal is female.

The present immunogenic composition and vaccines may be formulated with a pharmaceutically or veterinarily acceptable excipient, carrier, or diluent. The forms suitable for injectable commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

The present immunogenic composition or vaccines may include an adjuvant. The term "adjuvant" refers to a compound or mixture that is present in an immunogenic composition or vaccine and enhances the immune response to an antigen present in the immunogenic composition or vaccine. For example, an adjuvant may enhance the immune response to a polypeptide present in a vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant ASO21/ASO2 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block co-polymer adjuvants (e.g., CRL 1005), aluminum phosphates (e.g., $AlPO_4$), R-848 (a Thl-like adjuvant), imiquimod, PAM3CYS, poly (I:C), loxoribine, potentially useful human adjuvants such as BCG (bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

It is generally advantageous to formulate the present compositions in dosage unit form for ease of administration and uniformity of dosage. "Dosage unit form" as used herein refers to physically discrete units suited as unitary dosages for the animal subjects to the treated; each unit containing a predetermined quantity of the active material calculated to produce the desired therapeutic effect in association with the required pharmaceutical carrier. The specification for the dosage unit forms are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form. In some embodiments, a dose of the immunogenic composition or vaccine includes at least about 10 micrograms (preferably 100 micrograms) of one or more isolated polypeptides or peptides as disclosed herein.

Sterile injectable solutions may be prepared by incorporating the isolated polypeptide or peptide in the desired amount in an appropriate solvent with various of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient (i.e., lyophilized form of the active ingredient) plus any additional desired ingredient from a previously sterile-filtered solution thereof.

It also may be advantageous to add a stabilizer to the present compositions. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

CD47 Constructs and Compositions

CD47 constructs and composition based on these peptides might be of several kinds: 1) Synthetic peptides conjugated to a carrier protein; 2) Viral/bacterial vectors carrying sequences coding for the peptides; and 3) Recombinant phage constructs displaying the peptides. Phages displaying these peptides can be selected from phage display libraries as well as constructed by insertion of oligonucleotide sequences coding for the peptide into a phage vector.

Conjugation may occur via various methods. Peptide sequences disclosed herein may be modified to accommodate such methods. These include, but are not limited to, conjugation to lysine, cysteine, tyrosine, N and C termini, or biorthogonal reactions such as reactions with ketones, aldehydes, and azides. Exemplified methods include, but are not limited to, EDC and sulfo-SMCC conjugation chemistry.

After selection and optimization for binding, immunogenicity, stability, efficacy, etc., these sequences can be used in standard immunization protocols to induce endogenous antibody production of anti-CD47 antibodies. This in turn can mount an immune response against CD47-expressing cancerous cells, leading to tumor regression, suppression of cancer growth, and possible destruction of cancerous cells in vivo. These peptides may be delivered with carriers and adjuvants known in the art, be conjugated to immunogenic proteins, be delivered by bacteriophage particles, or delivered using other vaccine technologies.

The novel aspects of the sequences identified to date include sequences that would not immediately be considered hologous to CD47 immunogenic epitopes as well as epitopes that are not continuous. Thus, it would not have been obvious from current publications how to select or computationally generate and screen sequences for CD47-mimicking immunogenic sequences.

Antibodies and Other Binding Molecules

Also disclosed herein are isolated antibodies or other binding molecules that bind specifically to the peptides disclosed herein. For example, the antisera, antibodies, or other binding molecules, may include an isolated antibody that binds specifically to a polypeptide consisting of an amino acid sequence or motif of any of SEQ ID NOS:1-43. Preferably, the antisera, antibodies, or other binding molecules disclosed herein also bind specifically to CD47. The isolated antibody or binding molecule may be of any suitable isotype (e.g., IgG, IgM, IgE, IgD, IgA, and mixtures thereof). The antibodies may be polyclonal or monoclonal. The term "antibody or other binding molecule" refers to intact immunoglobulin molecules as well as to fragments thereof, such as Fab, F(ab')2, and Fv fragments, which are capable of binding an epitopic determinant. The antibodies or other binding molecules may be naturally occurring or synthetic (e.g., scFv). Other binding molecules may include antibody fragments (e.g., Fab fragments), coupled antibodies, and coupled antibody fragments. Antibodies or other binding molecules that bind the presently disclosed peptides and polypeptides can be induced or elicited using the intact peptide or a polypeptide comprising the intact peptide as an immunizing antigen. The polypeptide or oligopeptide used to immunize an animal can be derived from the translation of DNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide may then be used to immunize the animal. The antibodies or other specific binding molecules may be conjugated to a suitable therapeutic agent (e.g., a toxin) or a label. The antibodies may be modified for use in therapeutic or diagnostic methods.

Illustrative Embodiments

The following embodiments are illustrative and should not be interpreted to limit the scope of the claimed subject matter.

Embodiment 1. A method for obtaining an antigen for generating an immune response against CD47, the method comprising: (a) contacting a bacteriophage library with an anti-CD47 antibody; and (b) selecting bacteriophage from the library that bind specifically to the anti-CD47 antibody.

Embodiment 2. The method of embodiment 1, wherein the bacteriophage phage library is first contacted with a control antibody that is not an anti-CD47 antibody and bacteriophage phage that bind to the control antibody are removed from the bacteriophage phage library.

Embodiment 3. An isolated recombinant filamentous bacteriophage phage comprising an exogenous peptide, wherein the bacteriophage phage binds to an antibody against CD47.

Embodiment 4. The bacteriophage phage of embodiment 3, wherein the exogenous peptide is at least about five amino acids in length.

Embodiment 5. The bacteriophage phage of embodiment 3 or 4, wherein the exogenous peptide is at least about seven amino acids in length.

Embodiment 6. The bacteriophage phage of any of embodiments 3-5, wherein the exogenous peptide is at least about twelve amino acids in length.

Embodiment 7. The bacteriophage phage of any of embodiments 3-6, wherein the exogenous peptide is exactly twelve amino acids in length.

Embodiment 8. The bacteriophage phage any of embodiments 3-7, wherein the exogenous peptide comprises amino acid sequence GLSDYYRALAN (SEQ ID NO.:1) or a sequence having at least about 75% sequence identity thereto.

Embodiment 9. The bacteriophage phage of any of embodiments 3-8, wherein the exogenous peptide comprises amino acid sequence GITEYLRTINIG (SEQ ID NO:2) or a sequence having at least about 75% sequence identity thereto.

Embodiment 10. The bacteriophage phage of any of embodiments 3-9, wherein the exogenous peptide comprises amino acid sequence DYSLRLQYGHTY (SEQ ID NO:3) or a sequence having at least about 75% sequence identity thereto.

Embodiment 11. The bacteriophage of any of embodiments 3-10, wherein the exogenous peptide comprises amino acid sequence GLTDYLG (SEQ ID NO:4) or a sequence having at least about 75% sequence identity thereto.

Embodiment 12. The bacteriophage of any of embodiments 3-11, wherein the exogenous peptide comprises amino acid sequence EYVAPFNFLEWK (SEQ ID NO:5) or a sequence having at least about 75% sequence identity thereto.

Embodiment 13. The bacteriophage of any of embodiments 3-12, wherein the exogenous peptide comprises amino acid sequence YSDTSLSYMQRY (SEQ ID NO:6) or a sequence having at least about 75% sequence identity thereto.

Embodiment 14. The bacteriophage of any of embodiments 3-13, wherein the exogenous peptide comprises amino acid sequence GLGDRLSHGHTI (SEQ ID NO:7) or a sequence having at least about 75% sequence identity thereto.

Embodiment 15. The bacteriophage of any of embodiments 3-14, wherein the exogenous peptide is inserted within a gpVIII protein of the bacteriophage or the exogenous peptide is fused to a gpVIII protein of the bacteriophage.

Embodiment 16. The bacteriophage of any of embodiments 3-15, wherein the exogenous peptide is inserted within a gpIII protein of the bacteriophage or the exogenous peptide is fused to a gpIII protein of the bacteriophage Embodiment 17. The bacteriophage of any of embodiments 3-16, wherein the filamentous bacteriophage has no more than a single gene 8.

Embodiment 18. An immunogenic composition comprising: (a) the bacteriophage of any of embodiments 3-17; and (b) a suitable excipient, carrier, or diluent.

Embodiment 19. The composition of embodiment 18, further comprising an adjuvant.

Embodiment 20. A method for inducing an immune response against CD47 in a subject in need thereof, the method comprising administering the immunogenic composition of embodiment 18 or 19 to the subject.

Embodiment 21. A method for treating a subject having a cancer characterized by expression of CD47, the method comprising administering to the subject the immunogenic composition of embodiment 18 or 19.

Embodiment 22. An isolated polynucleotide encoding the bacteriophage of any of embodiments 3-17.

Embodiment 23. An isolated peptide comprising an amino acid sequence selected from a group consisting of SEQ ID NOS:1-7.

Embodiment 24. An immunogenic composition comprising the isolated peptide of embodiment 23 together with a suitable carrier, diluent, or excipient.

Embodiments 25. The immunogenic composition of embodiment 24 further comprising an adjuvant.

Embodiment 26. A method for inducing an immune response against CD47 in a subject in need thereof, the method comprising administering to the subject the composition of embodiment 24 or 25.

Embodiment 27. A vaccine for inducing an immune response against cancer cells comprising a peptide-based antigen mimic and a peptide carrier.

Embodiment 28. The vaccine of embodiment 27 wherein the peptide-based antigen mimic induces an immune response against an endogenous cellular protein.

Embodiment 29. The vaccine of embodiment 27 or 28 wherein the endogenous cellular protein is CD47.

Embodiment 30. The vaccine of any of embodiments 27-29 wherein the peptide-based antigen mimic is at between 6 and 30 amino acids in length.

Embodiment 31. The vaccine of any of embodiments 27-30 wherein the peptide-based antigen mimic is linked to a peptide carrier.

Embodiment 32. The vaccine of any of 31 wherein the peptide carrier is a protein, virus, bacteriophage, microscopic particle, compound, or an expression vector that encodes the peptide-based antigen mimic.

Embodiment 33. The vaccine of any of embodiments 27-31 wherein the peptide-based antigen mimic is selected from at least one of the following peptides: GLSDYYRALAN (SEQ ID NO:1), GITEYLRTINIG (SEQ ID NO:2), DYSLRLQYGHTY (SEQ ID NO:3), GLTDYLG (SEQ ID NO:4), EYVAPFNFLEWK (SEQ ID NO:5), YSDTSLSYMQRY (SEQ ID NO:6), GLGDRLSHGHTI (SEQ ID NO:7), DYSLRLQYGHTYGGGS (SEQ ID NO:8), EYVAPFNFLEWKGGGS (SEQ ID NO:9), GISDYIGGKHHVGGGS (SEQ ID NO:10), GITDFLSWSWQAGGGS (SEQ ID NO:11), GITEYLRTINIGGGGS (SEQ ID NO:12), GKLANIAGGGS (SEQ ID NO:13), GLSDYYYRALANGGGS (SEQ ID NO:14), GLTDYLGGGGS (SEQ ID NO:15), YSDTSLSYMQRYGGGS (SEQ ID NO:16), GITEYLRTINIGGGGS (SEQ ID NO:17), GITEYLRTINIGK (SEQ ID NO:18), GITEYLRTINIGGGGSK (SEQ ID NO:19), GINITRLYETIG (SEQ ID NO:20), SGGGGINITRLYETIG (SEQ ID NO:21), GITEYLRTIGLSDYYYRA (SEQ ID NO:22), GLSDYYYRALAN (SEQ ID NO:23), GLSDYYYRALANGGGS (SEQ ID NO:24), GLSDYYYRALANK (SEQ ID NO:25), GLSDYYYRALANGGGSK (SEQ ID NO:26), NALARYYYDSLG (SEQ ID NO:27), SGGGNALARYYYDSLG (SEQ ID NO:28), DYSLRLQYGHTYGGGS (SEQ ID NO:29), DYSLRLQYGHTYK (SEQ ID NO:30), DYSLRLQYGHTYGGGSK (SEQ ID NO:31), YTHGYQLRLSYD (SEQ ID NO:32), SGGGYTHGYQLRLSYD(SEQ ID NO:33), GLTDYLGC (SEQ ID NO:34), GLTDYLGGGGSC (SEQ ID NO:35), GITEYLRTINIGC(SEQ ID NO:36), GITEYLRTINIGGGGSC (SEQ ID NO:37), GLSDYYYRALANC (SEQ ID NO:38), GLSDYYYRALANGGGSC (SEQ ID NO:39), DYSLRLQYGHTYC (SEQ ID NO:40), and DYSLRLQYGHTYGGGSC (SEQ ID NO:41).

Embodiment 34. A method for treating cancer comprising administering to a patient an effective amount of the vaccine composition of any of any of embodiments 27-33.

Embodiment 35. The method of embodiment 34 wherein the effective amount of vaccine is sufficient to inhibit growth of cancerous cells.

Embodiment 36. The method of embodiment 34 or 35 wherein the cancerous cells overexpress CD47.

EXAMPLES

The following Examples are illustrative and are not intended to limit the scope of the claimed subject matter.

Example 1—Generation and Characterization of Phage-CD47 Peptide Fusions

In general, phage-peptide constructs can be obtained either via molecular cloning or they can be isolated from phage libraries for binding to a specific target. Although the SIRPα-binding site on CD47 is known, its sequence cannot be used for phage cloning because the epitope is not continuous. Instead, phage-CD47 peptide fusions will be selected from a phage display library which is a multibillion blend of pre-engineered phages displaying random peptides. The proposed library is constructed in a filamentous fd phage vector type 8. Phages in this library display fusion peptides in each copy of the major phage coat protein VIII, resulting in presentation of 4000 peptide copies per phage particle. Such densely displayed epitopes are presented in a highly organized manner and are properly spaced for binding to B cell receptors. Repetitive, highly organized epitope patterns usually permit cross-linking activation of B cell receptors, which provides robust antibody responses. This library was chosen since phages displaying high peptide copy numbers were shown to stimulate stronger immune responses to fusion peptides. The library contains $2 \times 10^9$ different phage clones, providing incredible diversity for finding phages displaying peptides that resemble SIRPα-binding site on CD-47 or mimic the binding epitope functionally.

The phage selection procedure is straightforward and includes: (1) incubation of the phage library with a specific target which is an anti-CD47 antibody in our case; (2) removal of phages that do not bind to the target; and (3) recovery of phages bound to the target specifically. These steps, which comprise one selection round, are repeated several times (typically three to five) to enrich for specific target-binding phage. At completion of the selection process, phage DNAs are sequenced and translated to determine sequences of peptides displayed on the phage that bind to anti-CD47 antibodies.

Two types of blocking anti-CD47 antibodies, B6H12 and BRIC126, will be used as selection targets. Both antibodies are available commercially and are human mAbs with proven anti-cancer activity. BRIC126 antibody also has been shown to be canine cross-reactive, which will allow the use of our identified phage-CD47 for testing in dogs with spontaneous lymphomas in our future phage-CD47 vaccination studies. Prior to selection on the target CD47 antibodies (B6H12 or BRIC126), a naïve phage library will be pre-selected on non-blocking CD47 antibodies, to remove phage clones that bind to non-blocking antibody domains. The depleted library then will be incubated with the blocking CD47 antibodies immobilized on magnetic beads coated with protein G. Phage clones with no affinity to CD47 antibody will remain unbound and will be removed by repeated washings. CD47 antibody-bound phages will be recovered by elution and amplified in bacteria. Enrichment in CD47 antibody-binding phage clones will be achieved in four subsequent selection rounds. The entire phage outputs ($10^5$-$10^6$ phage clones) obtained after selection rounds three and four will be subjected to next generation sequencing (NGS) in order to identify target-specific phage clones. The obtained sequences will be analyzed for similarity to CD47 protein using BLAST database. The selected candidate phages will be further characterized for binding specificity to the target anti-CD47 antibodies in ELISA format using individual phage clones as detector agents immobilized on ELISA plates.

Example 2—Phage-Peptide Constructs for Stimulation of Anti-Cancer Immune Responses Against CD47

INTRODUCTION

The long-term goal of this study is to generate effective phage-based products for active immunization against CD47 receptor, a target that is widely used for development of immunotherapies against human and canine cancers. CD47 is a cell surface protein that belongs to the immunoglobulin superfamily and demonstrates high homology in the exposed extracellular-domain between species. (See FIG. 1). CD47 binds several proteins including signal-regulatory protein-alpha (SIRPα) expressed on phagocytes. Binding of CD47 to SIRPα leads to inhibition of phagocytosis. (See FIG. 2). In this respect, CD47 plays a role of a "don't eat me" signal for phagocytic cells, making cells expressing CD47 resistant to phagocytosis. Many types of cancers escape clearance by the immune system by up-regulation of CD47 expression. One strategy to disarm the "don't eat me" signal on cancer cells is to block CD47 with neutralizing antibodies, preventing the CD47-SIRPα interaction. The present study is designed to generate and characterize phage-CD47 constructs to stimulate production of blocking antibodies against extracellular CD47 epitopes using phage display technology.

We hypothesize that active immunization against CD47 using phage CD47-mimicking constructs will stimulate production of neutralizing CD47 antibodies, which will block CD47-SIRPα interactions and stimulate phagocytosis of cancer cells. To test this hypothesis, we had the following goals: 1) Enrich peptide populations with increased binding to CD47 monoclonal antibodies; 2) Identify displayed peptide sequences by Sanger and Next Generation Sequencing (NGS); and 3) Test binding of synthesized peptides to CD47 monoclonal antibodies.

Enrichment of Peptides Binding CD47 mAbs

Figure 3:
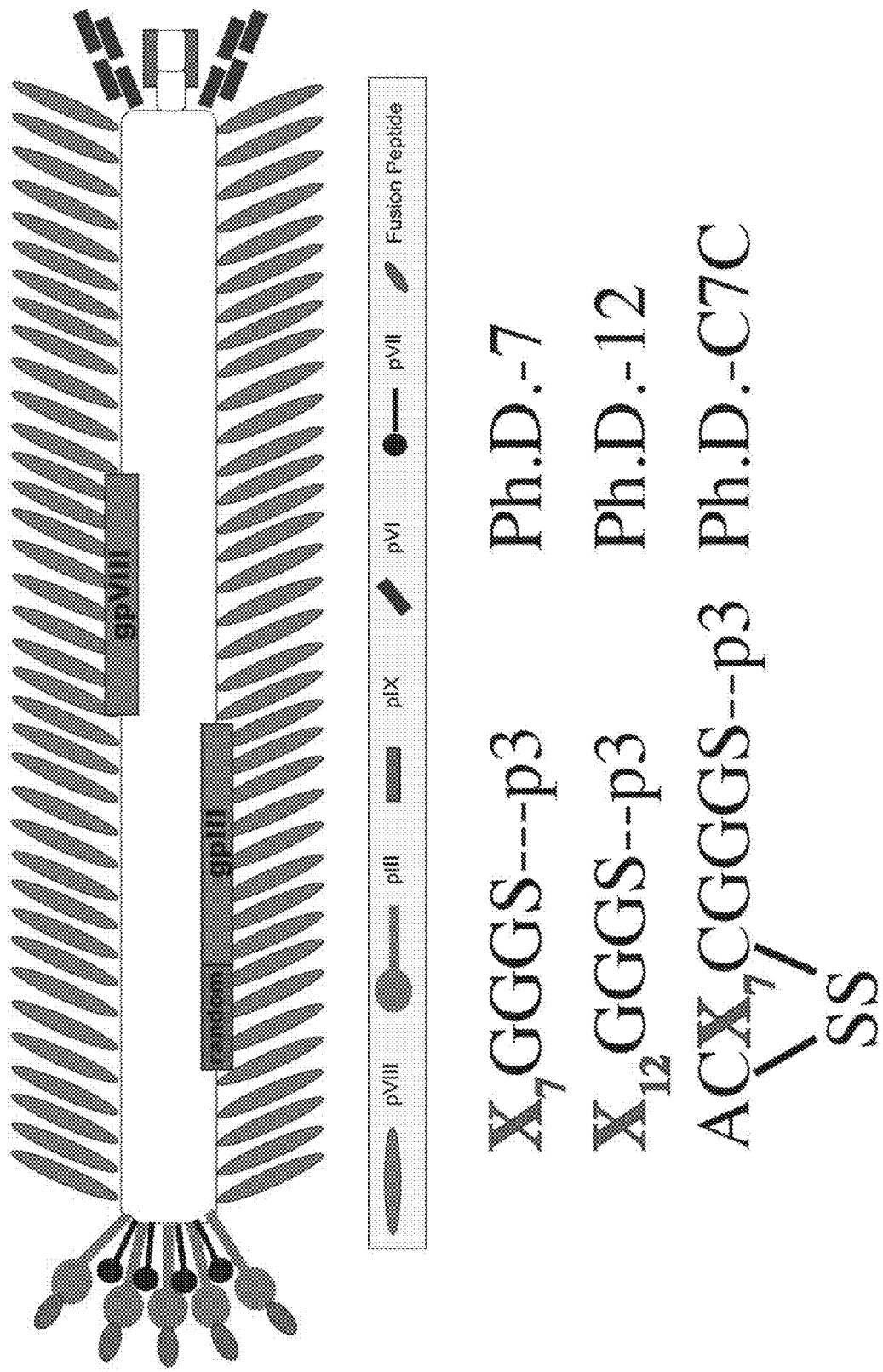
FIG. 3. Schematic structure of recombinant phage with modified gpIII protein. Illustrated phage libraries include two linearly presenting libraries $X_7$GGGS-p3 (SEQ ID NO:49; Ph.D.-7); $X_{12}$GGGS-p3 (SEQ ID NO:50; Ph.D.-12), and a loop constrained library AC(S)$X_7$C(S)GGGS-p3 (SEQ ID NO:51; Ph.D.-C7C).
Figure 4:
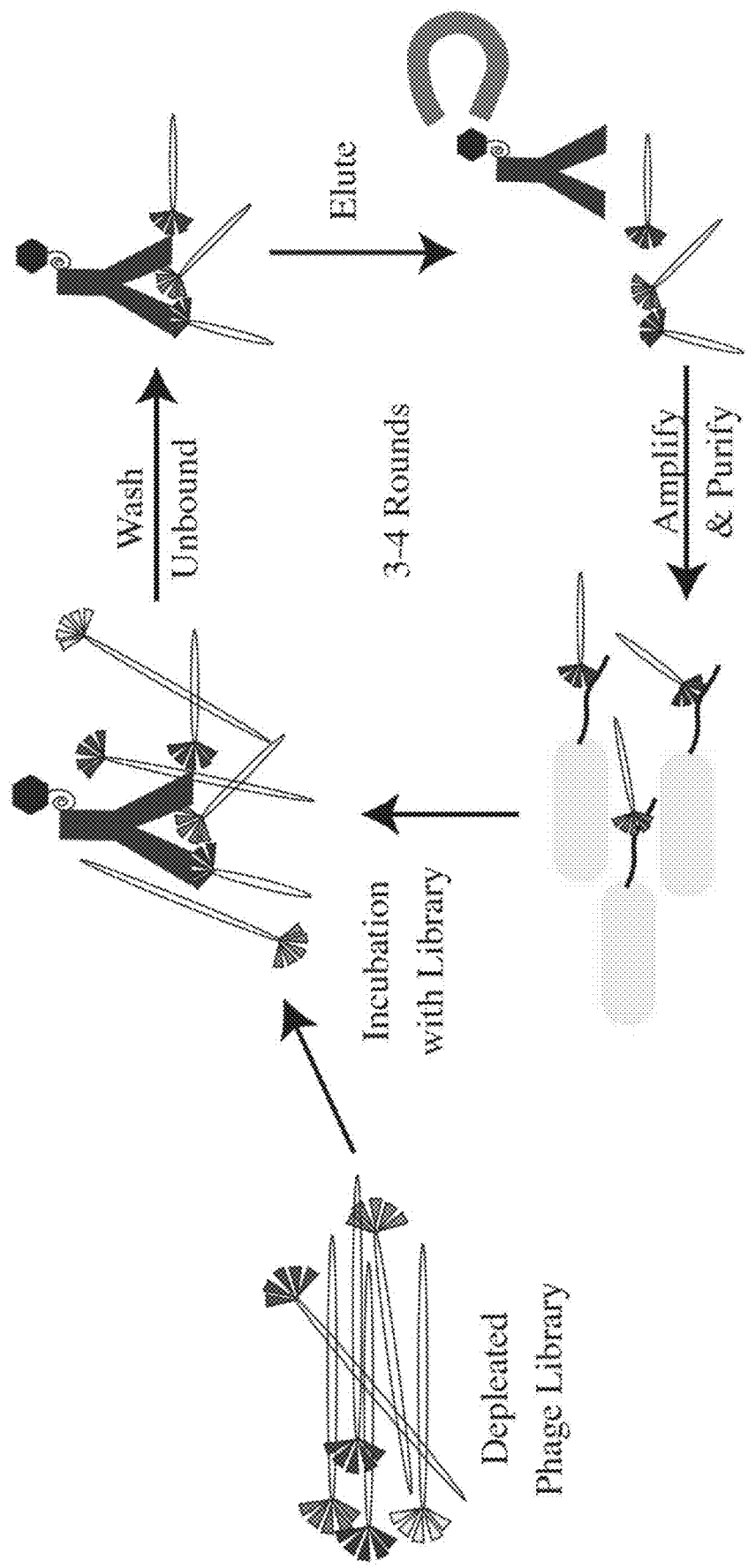
FIG. 4. Schematic illustration of phage selection and enrichment based on binding to anti-CD47 antibody.

Phage-CD47 constructs were obtained via selection from phage display libraries for binding to CD47 monoclonal antibodies (mAbs) as selection targets. Two types of CD47 mAbs (BRIC126 & B6H12) and three commercially-available phage display libraries (Ph.D-C7C, Ph.D.-7, & Ph.D.-12) were used for enrichment of CD47-mimicking peptide sequences. (See FIG. 3 and FIG. 4).

Figure 5:
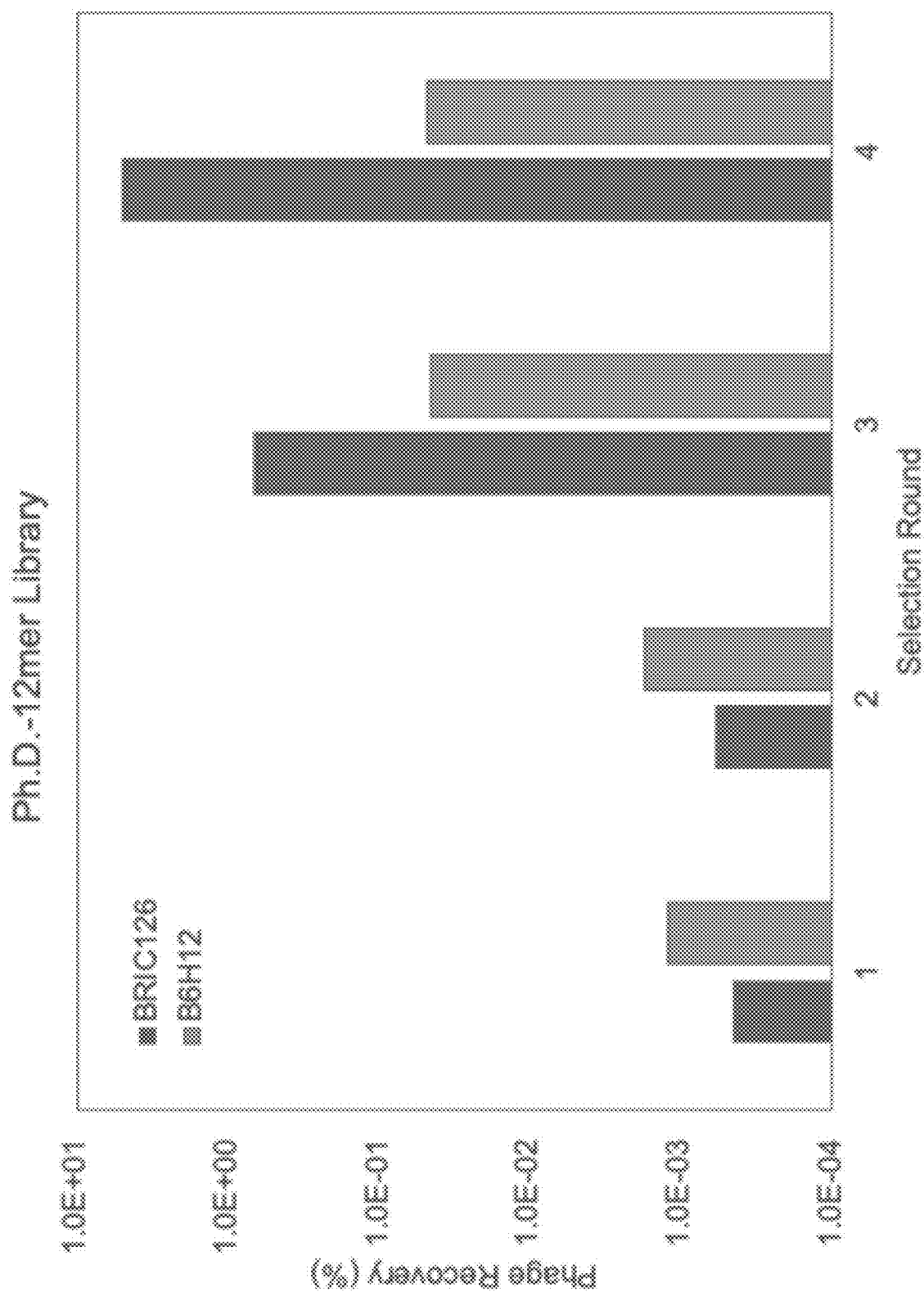
FIG. 5. Demonstrates an increase in yield after 3-4 selection round for the Ph.D.-12mer library.
Figure 6:
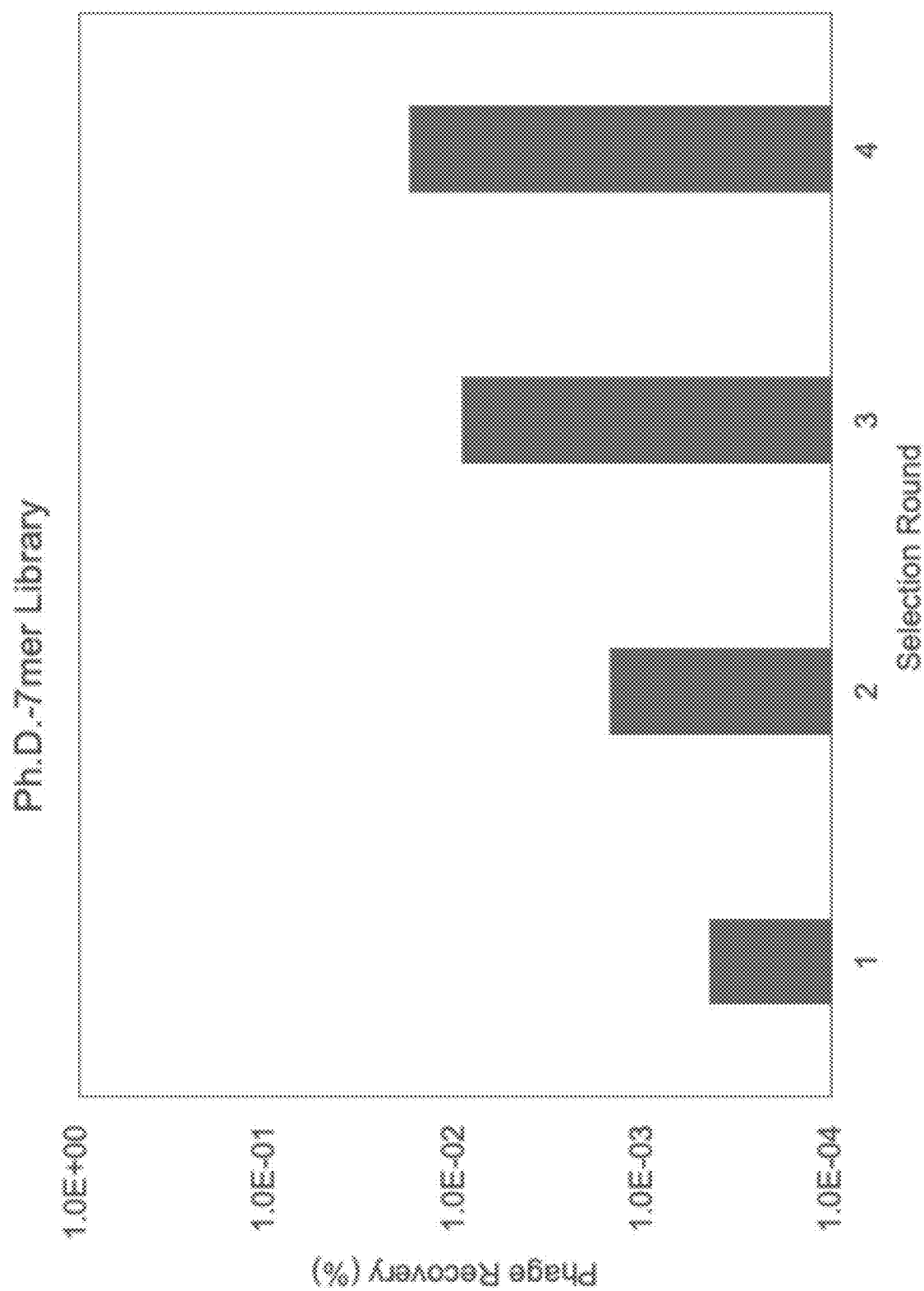
FIG. 6. Demonstrates an increase in yield after 3-4 selection round for the Ph.D.-7mer library.
Figure 7:
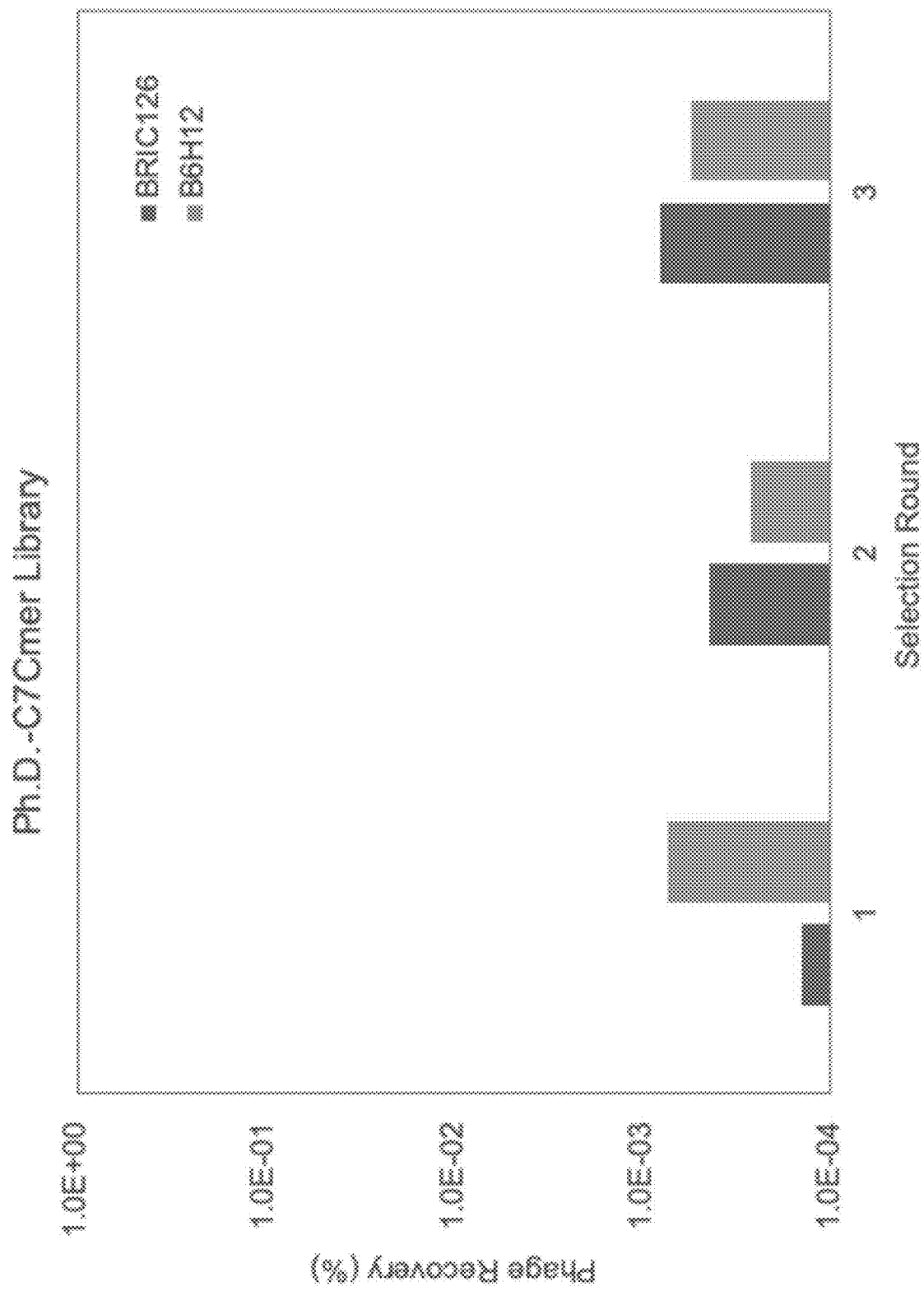
FIG. 7. Demonstrates no increase in yield after 3-4 selection round for the Ph.D.-C7Cmer library.

We studied the difference in library conformation, comparing the loop-constrained Ph.D.-C7C library with the non-constrained, linear Ph.D.-7 library. (See FIG. 3). After 3-4 rounds of selection with each 7-mer and 12-mer library (see FIG. 4), we observed a successive increase in recoverd phage yield from each of the linear libraries subbesting population enrichment of phages. (See FIG. 5 and FIG. 6). No increase in yield was observed in the loop-constrained library suggesting no enrichment of phages. (See FIG. 7).

Identification of Peptide Sequence by NGS on MiSeq

Figure 8:
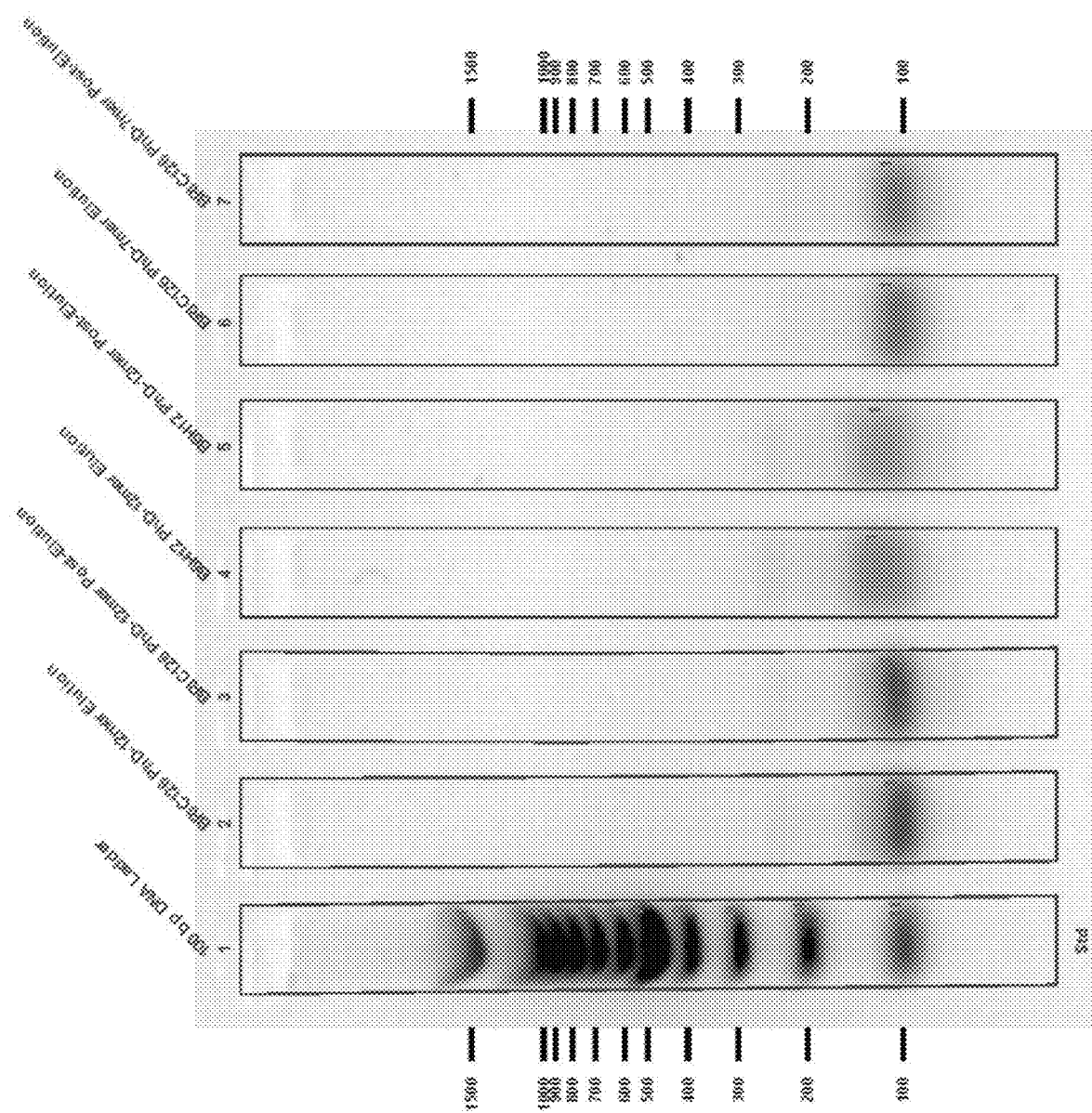
FIG. 8. Gel electrophoresis of amplicons comprising phage sequence encoding exogenous peptide.
Figure 9:
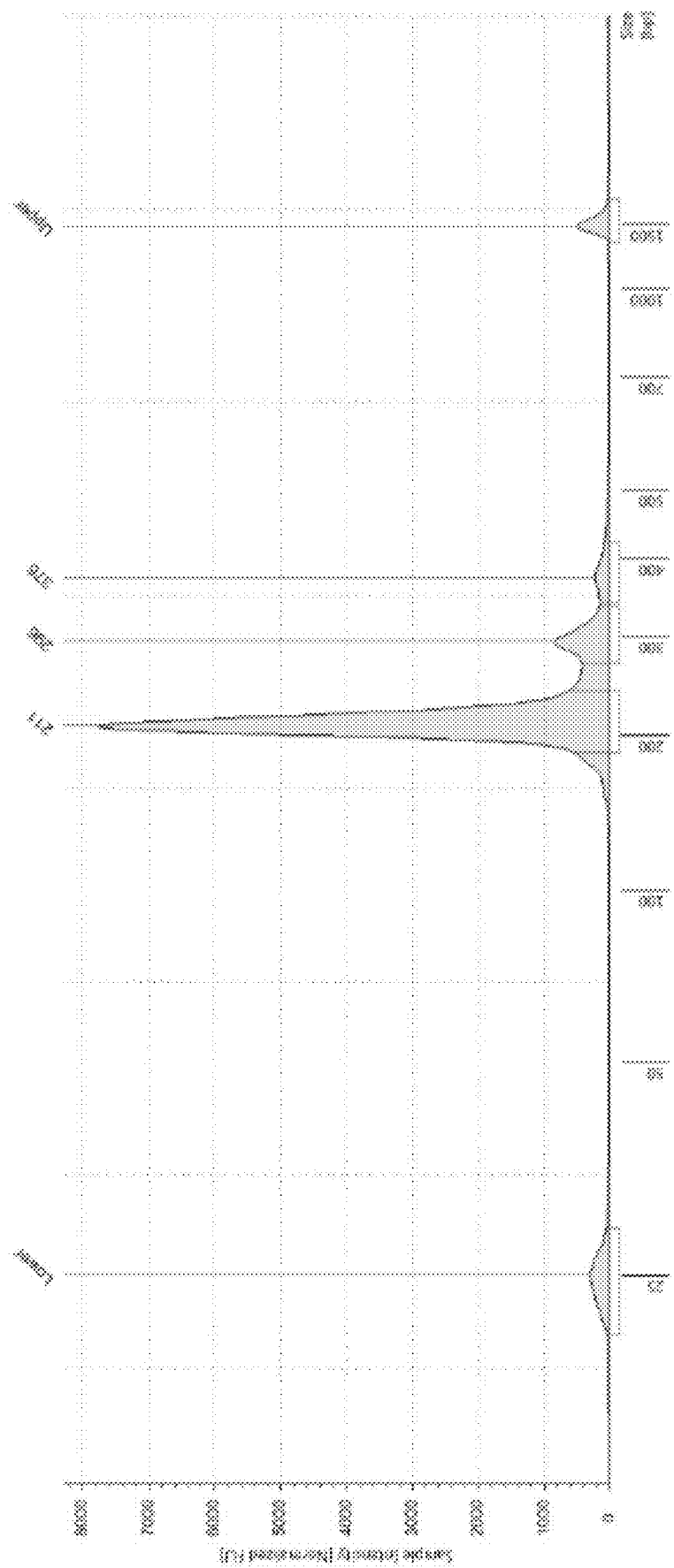
FIG. 9. Sample intensity versus amplicon size.

After the final round of each selection, ~80 clones were randomly isolated for Sanger sequencing and the unamplified portion of each fraction amplified by qPCR with gp3-specific primers for amplicon-specific targeted next generation sequencing (NGS) on a MiSeq. (See FIG. 8 and FIG. 9).

Figure 10:
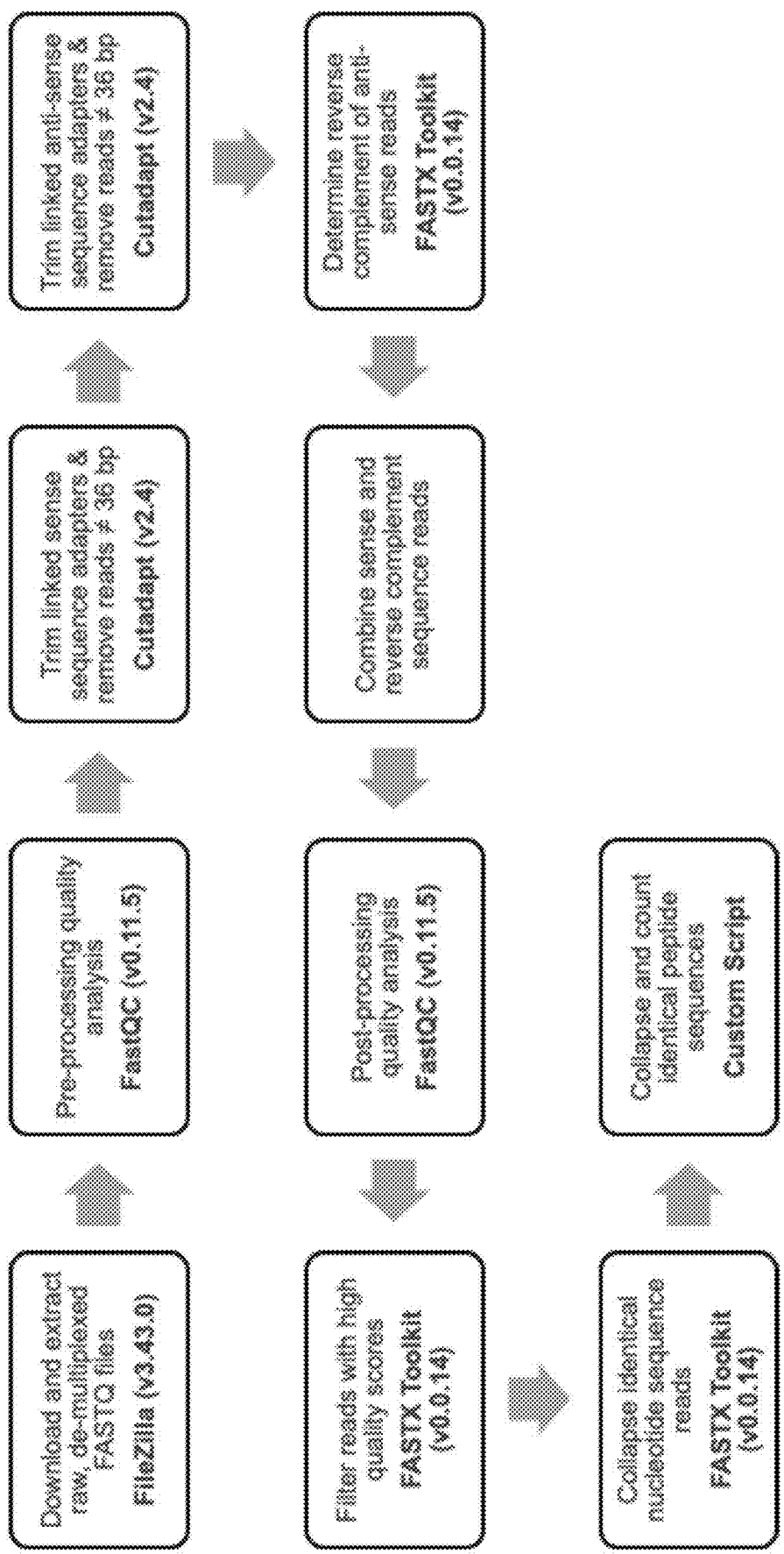
FIG. 10. Illustration of p3-targeted NGS workflow.
Figure 12:
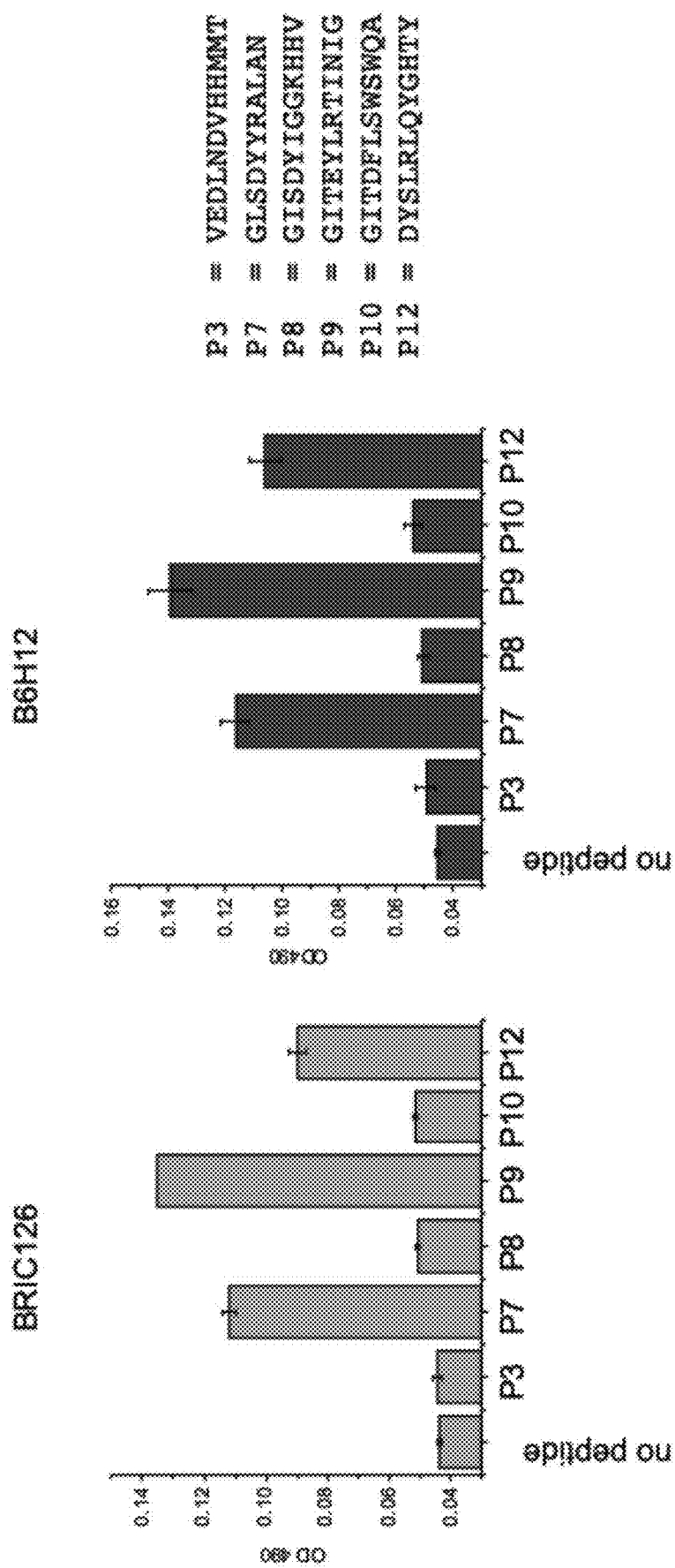
FIG. 12. Binding of peptides P3 (SEQ ID NO:52), P7 (SEQ ID NO:1), P8 (SEQ ID NO:53), P9 (SEQ ID NO:2), P10 (SEQ ID NO:54), and P12 (SEQ ID NO:3) to anti-CD47 mAbs as tested by indirect ELISA.

Following amplicon purification and multiplex adapter ligation, samples were pooled and sequenced on an Illumina MiSeq using a 150 bp single-end (SE) reaction kit. Raw, demultiplexed FASTQ files were obtained and analyzed using a p3-targeted NGS workflow. (See FIG. 10).

Performance of the p3-targeted NGS workflow produced ~18,000 unique peptide sequences from a total of ~16 million sequence reads as summarized in the table of FIG. 11.

Evaluation of CD-47 Mimicking Peptide Epitopes

Sequences were analyzed for their ability to map to the surface of CD47 crystal structures obtained from the protein data bank (PDB) using the PepSurf epitope mapping algorithm. Candidate peptides were identified based on their high occurrence in the population of phage clones or were found at the proposed interaction site between CD47 and SIRPα. Individual peptide sequences that compose the interaction consensus cluster were identified by manually verifying peptides that are either 1) located at a site interaction based on the 3D model or 2) shared a significant number of residues with known interaction sites of CD47 with SIRPα.

Twelve peptides were tested for binding to anti-CD47 mAbs by indirect ELISA. Three peptides with relatively high binding activity to both CD46 mAbs suggest the peptides may mimic a discontinuous structural epitope. (See FIG. 12).

CONCLUSION

Here we biopanned multiple p3-type phage display libraries against two CD47 monoclonal antibodies to identify peptide candidates that could be used to induce an active immune response against the CD47-SIRPα interaction site. NGS and Sanger sequencing were used to identify panels of peptide candidates. Three peptide candidates were identified with binding activity towards anti-CD47 mAb. Peptides mapped to the surface of CD47 and block SIRPα interactions.

Example 3—Optimization of Phage-Peptide Constructs for Stimulation of an Anti-Cancer Immune Response Against CD47

INTRODUCTION

CD47 is a cell surface protein that belongs to the immunoglobulin superfamily and demonstrate high homology in the exposed extracellular-domain between species. (See FIG. 1). CD47 binds several proteins including signal-regulatory protein-alpha (SIRPα) expressed on phagocytes. (See FIG. 2). Binding of CD47 to SIRPα leads to inhibition of phagocytosis. (See FIG. 2). In this respect, CD47 μlays a role of a "don't eat me" signal for phagocytic cells, making cells that express CD47 resistant to phagocytosis. Many types of cancer escape clearance by the immune system by up-regulation of CD47 expression. One strategy to disarm the "don't eat me" signal on cancer cells is to block CD47 with neutralizing antibodies in order to prevent the CD-47-SIRPα interaction. (See FIG. 2).

One long-term goal of our project is to develop an active immunization platform using phage-constructs to stimulate production of blocking antibodies against CD47 epitopes. In our previous studies described in Example 1 and Example 2, we identified a panel of peptides that interact with two different CD47 monoclonal antibodies from three different phage display libraries. In the present study, our goal was to optimize and maximize the presentation of the identified peptides on the surface of filamentous phages using two different approaches: 1) chemical conjugation of CD47 antigenic peptides to the surface of phage particles 2) genetic modification of phages by introducing peptide fusions of identified CD47 antigenic peptides into several hundred copies of the p8 major coat protein.

Methods

A total of 26 different peptides were designed and synthesized for chemical conjugation to phage particles. Eighteen of these peptides were conjugated using EDC chemistry. (See FIG. 13).

Eight peptides were conjugated using sulfo-SMCC chemistry. Three CD47 antigenic peptides identified from biopanning experiments with highest activity were synthesized in 6 different variations and conjugated to phages using EDC chemistry to optimize presentation of CD47 epitopes to immune cells. Four CD47 antigenic peptides were synthesized with a C-terminal cysteine residue to allow conjugation to phages using sulfo-SMCC chemistry. (See FIG. 14).

A total of 6 different genetically engineered phages were constructed on the f88-4 vector to evaluate the effect of different peptide linkers (proline-rich, glycine-rich, and alpha-helical spacers) to display CD47 antigenic peptides on the surface of phages. All phage-peptide constructs were evaluated using a CD47 indirect ELISA versus unmodified phages. (See FIG. 15).

Results

We constructed 6 different variants of the DYSLRLQYGHTY (SEQ ID NO:3) peptide for display on the f88-4 phage vector which will display the recombinant peptide on ~10% of the p8 major coat protein after induction with 1 mM IPTG. All genetic constructs failed to bind CD47 antibody although expression of the recombinant protein on the surface of the phage was not verified by PAGE and Western Blotting. (See FIG. 16).

To identify candidate peptides that could be used for construction of phage-peptide conjugates, we synthesized 11 peptides that were biotinylated at the C-terminus of the peptide. Three of these peptides identified by the first three amino acid residues (DYS, GIT, and GLS), demonstrated significant binding to either CD47 antibody compared to no peptide or a random peptide control. (See FIG. 17). These peptides were used for conjugation to phages by either EDC or sulfo-SMCC chemistry.

First, we tested conjugating different variants of the top three peptides to wild type phages using EDC chemistry. With only one conjugate demonstrating binding to CD47. (See FIG. 18).

Next, we tested conjugation of different variants to wild type phages using sulfo-SMCC chemistry. Here, two conjugates demonstrated binding to CD47 on ELISA. (See FIG. 19).

Conclusions

In summary, we tested attachment of several different variants of CD47 antigenic peptides by different chemical conjugation methods and tested the effect of multiple commonly used peptide linkers to appropriately display peptides on the surface of the phage constructs for interaction with immune cells.

Example 4—Generation of Phage-Peptide Conjugates for Immunization of Dogs Using EDAC Protocol Materials 2 preps with M13 vector phage were combined to obtain 1000 μl with 11.84 mg/ml protein (phage concentration: $6.5\times10^{12}\times11.84=7.7\times10^{3}$ vir/ml); GLS b peptide (GLSDYYYRALANGGGS (SEQ ID NO: 14)-Acid peptide; New England Peptide, 1 mg/vial); EDAC (Millipore, Cat. #341006-5GM); $H_2O$ (adjusted to pH 5.0 with $H_3PO_4$) and filter sterilized; PBS, pH 7.2; Thermo Scientific; Product No. 28372; Cold sterile PBS pH 7.4-7.5; to prepare 7 L: NaCl—56 g; KCl—1.4 g; $Na_2HIPO_4$—10.08 g; $KH_2PO_4$—1.68 g; and Slide-A-Lyzer Dialysis Cassettes 10K MWCO, 0.5-3 ml, Gamma irradiated (Thermo Scientific).

Procedure

1. Take 4 vials with 1 mg peptide/vial (GLS b; New England Peptide) and add 1000 μl $H_2O$ pH 5.0 to each vial to obtain final peptide concentration 1 mg/ml.

2. Dilute EDAC (Millipore, Cat. #341006-5GM) 50 mg EDAC+500 μl $H_2O$, pH 5.0.

3. Dilute phage vector to obtain ~1 mg/ml phage. For 2 dogs we need 4 ml. 337.84 μl phage+3662 μl $H_2O$ pH 5.0=4000 μl.

4. Mix components in the following order: 4 ml phage+400 μl of EDAC+4 ml peptide.

5. Incubate mix for 4.5 h at RT with gentle rotation.

6. Transfer phage-peptide conjugate to Slide-A-Lyzer Dialysis Cassettes 10K MWCO 0.5-3 ml, Gamma irradiated (Thermo Scientific), ~3 ml per cassette, 3 cassettes total, using 5 ml syringe with 21×1½" needle.

7. Put cassettes in a beaker with 2 L cold PBS (sterile) and perform dialysis for ~40 hrs in cold room. Change dialysis buffer 2 times.

8. Removed phage-peptide conjugates from dialysis cassettes, combine and store in refrigerator before injection.

9. Check the prep for sterility as described in Example 6 below.

Example 5—Generation of Phage-Peptide Conjugates for Immunization of Dogs Using Sulfo-SMCC Protocol Materials 2 preps with M13 vector phage were combined to obtain 1000 µl with 13.196 mg/ml protein (phage concentration $6.5 \times 10^{12} \times 13.196 = 8.6 \times 10^{13}$ vir/ml); GIT c4 peptide (GIT-EYLRTINIGGGSC (SEQ ID NO: 37)-Amide peptide; New England Peptide, 1 mg/vial); DYS c8 peptide (DYS-LRLQYGHTYGGGSC (SEQ ID NO: 37)-Amide peptide; New England Peptide 1 mg/vial); Sulfo-SMCC cross linker (Thermo Scientific™ No-Weigh™ Sulfo-SMCC; Cat #A39268); H$_2$O (sterile-filtered, Sigma, W3500); PBS, pH 7.2; Thermo Scientific; Product No. 28372; Cold sterile PBS pH 7.4-7.5; to prepare 7 L: NaCl—56 g; KCl—1.4 g; Na$_2$HPO$_4$—10.08 g; KH$_2$PO$_4$—1.68 g; Spin Desalting Columns (Thermo Scientific™ Zeba™ Spin Desalting Columns, 5 mL; Cat #89891); and Slide-A-Lyzer Dialysis Cassettes 10K MWCO, 0.5-3 ml, Gamma irradiated (Thermo Scientific).

Procedure

1. Take 3 vials of each peptide (GIT c4 GITEYLR-TINIGGGSC (SEQ ID NO: 37)-Amide and DYS c8 DYSLRLQYGHTYGGGSC (SEQ ID NO: 41)-Amide; New England Peptide) with 1 mg peptide/vial and add 1000 µl 120 (sterile-filtered, Sigma, W3500) to each vial to obtain final peptide concentration 1 mg/ml. Total—3 ml of each peptide with 1 mg/ml.

2. Dilute phage vector in conjugation buffer (PBS, pH 7.2; Thermo Scientific; Product No. 28372) to obtain ~1 mg/ml phage. For 4 dogs we need 12 ml. This is 6 ml per phage-peptide conjugate to inject 2 dogs.

3. Dilute Sulfo-SMCC cross linker (Thermo Scientific™ No-Weigh™ Sulfo-SMCC; Cat #A39268):—take 2 vials with 2 mg cross linker per vial and add 200 µl H$_2$O (sterile-filtered, Sigma, W3500) to each vial. If the Sulfo-SMCC is not dissolved completely, warm for several minutes at 50° C.

4. Add 120 µl cross linker to each tube with 6 ml phage (from step 2).

5. Incubate reaction mixture for 30 minutes at RT with gentle rotation.

6. Remove excess cross linker using a desalting column (Thermo Scientific™ Zeba™ Spin Desalting Columns, 5 mL; Cat #89891) equilibrated with PBS buffer (PBS, pH 7.2; Thermo Scientific; Product No. 28372); 3 columns per sample (2 ml per column). Desalting column preparation: a. Twist off the column's bottom closure and loosen cap. Place column in a collection tube; b. Centrifuge column at 1000×g for 2 minutes to remove storage solution. Place a mark on the side of the column where the compacted resin is slanted upward. Place column in centrifuge with the mark facing outward in all subsequent centrifugation steps; c. Add 2.5 ml of PBS buffer (pH 7.2; Thermo Scientific; Product No. 28372) to the column; d. Centrifuge at 1000×g for 2 min to remove buffer; e. Repeat Steps c and d two or three additional times, discarding buffer from the collection tube; and f. Place column in a new collection tube, remove cap and slowly apply sample to the center of the compact resin bed.

7. Add 2 ml mixture from step 5 per column.

8. Centrifuge column at 1000×g for 2 min to collect phage-cross linker sample.

9. Combine phage-cross linker samples from 3 columns.

10. Add 3 ml of GIT c4 peptide to 6 ml of phage cross-linker.

11. Add 3 ml of DYS c8 peptide to 6 ml of phage cross-linker.

12. Incubate reaction mixtures from steps 10 and 11 for 30 min at RT with gentle rotation.

13. Transfer phage-peptide conjugates to Slide-A-Lyzer Dialysis Cassettes 10K MWCO 0.5-3 ml, Gamma irradiated (Thermo Scientific), ~3 ml per cassette using 5 ml syringe with 21×1½" needle.

14. Put 3 cassettes per beaker with 2 L cold PBS (sterile) and perform dialysis for ~14 hrs in cold room or refrigerator. Change buffer during dialysis 2 times.

15. Removed phage-peptide conjugates from dialysis cassettes using 5 ml syringe with 21×1½" needle, combine and store in refrigerator before injection.

16. Check the prep for sterility.

Example 6—Testing Phage-Peptide Conjugates for Sterility

Materials

LB agar medium 6 plates warmed for 30 minutes at 37° C.; LB broth; Phage-peptide conjugates samples: #1, 2, and 3 (see below); Sterile spreaders; and Culture plate rotator.

Procedure

The peptide conjugates were mixed by vortex and 10 µl of each conjugate was mixed with 200 µl of LB broth and spread evenly across the LB plate by rotating the plate. The plates were allowed to dry, then inverted and placed in the 37° C. incubator for 27 hours. Each sample was plated in duplicate.

Observation after 27 hours: no growth of bacteria.

Example 7—Immunization of Dogs with Phage-Peptide Conjugates

Dogs 2 dogs were immunized per conjugate×3 conjugates=6 dogs total.

Conjugates (3 total)

1 is GLS b peptide (GLSDYYYRALANGGGS (SEQ ID NO: 14)-Acid); #2 is GIT c4 peptide (GITEYLR-TINIGGGSC (SEQ ID NO: 37)-Amide); and #3 is DYS c8 peptide (DYSLRLQYGHTYGGGSC (SEQ ID NO: 41)-Amide).

Preparation of Injections

After dialysis, we obtained ~8 ml of each conjugate to be used for 2 dogs, 4 ml per dog. This volume was split: 3 ml for IM injection and 1 ml for ID injection per dog. We used 21×1½" needle to pull the conjugates into syringes, then changed the needle as follows to inject dogs. We used 5 ml syringe with 25×⅝ needle for IM injections. We used 3 ml syringe with 21×1 needle for ID injections. Dogs were injected as in the IACUC protocol.

Example 8—CD47-Mimicking Phage-Peptide Constructs for Anti-Cancer Vaccinations Abstract One long-term goal of this study is to generate effective phage-based products for active immunization against CD47, a target that is widely used for development of immunotherapies against human and canine cancers. CD47 is a major signaling molecule providing a "don't eat me" indication to phagocytic cells, which makes cells expressing CD47 resistant to phagocytosis. Many cancer types commonly overexpress CD47 as a mechanism to escape immune detection and clearance by the innate immune system. As demonstrated using CD47 monoclonal antibody therapy, blockade of CD47-SIRPα signaling axis allows phagocytic cells to recognize cancer cells and eliminate them through several mechanisms including removal by cells of the innate immune system. Currently, several active clinical trials using passive immunotherapy of CD47 are on-going with only mild toxicities in a broad range of cancer types. The goal of our program is to develop and characterize an alternative pathway for stimulating production of anti-CD47 neutralizing antibodies by active immunization using phage-peptide constructs. During our previous studies, we have successfully identified several peptides using phage display that interact with two different CD47 monoclonal antibodies and optimized methods to conjugate these peptides on the surface of the filamentous bacteriophage M13 serving as a backbone to deliver hundreds to thousands of peptides fused to its surface. We are currently testing three phage-peptide conjugates for their antigenicity in a canine model to validate that anti-CD47 IgGs are produced and these IgGs will block the CD47-SIRPα signaling axis. We hypothesize that active immunization against CD47 using the CD47-mimicking phage-peptide constructs described above will stimulate production of neutralizing CD47 antibodies that produce blocking of the CD47-SIRPα signaling axis and will ultimately enable activation of the innate immune response to remove cancer cells overexpressing CD47. To prove this hypothesis, we seek to test the following three specific aims in the scope of this project: 1) CD47 is overexpressed in several types of canine cancer, 2) immunization of CD47-mimicking phage-peptide constructs in a mouse model with an established melanoma tumor will produce a reduction in tumor volume (therapeutic response), and 3) immunization of CD47-mimicking phage-peptide constructs in a mouse model prior to engraftment of a melanoma tumor will prevent growth in tumor volume and provide protection against tumor formation (prophylactic response). As our first study was aimed at identifying peptides and developing optimized constructs that produce an immune response towards CD47, our current study provides proof-of-concept data of efficacy of our CD47-mimiking phage-peptide constructs to provide therapeutic activity towards a mouse allograft tumor model of melanoma and allows us to identify/characterize the CD47 expression in our patient population at the AUCVM to enable translation into a clinical trial in future programs. Development and validation of these assays for characterization of CD47 in the canine population will allow us to start initiating contacts with clinical oncology research scientists and identifying potential patient populations that could receive the most benefit.

Background and Significance

Mechanisms of Tumor Immune Escape. Both innate and adaptive immune responses have been recognized, for many decades, as a major mechanism for the detection and elimination of neoplastic cells in patients (Oncogene 2008, 27 (45): 5868). The immune system essentially functions by discriminating between self and non-self particles. Whether the particle is a virus or a multi-cellular organism, when a non-self particle is identified, the immune system is responsible for effectively removing it from the host to prevent any damage. To the immune system, neoplastic cells are neither truly self nor non-self, but detected as altered self particles making clearance of mutated cells possible. To successfully grow into a clinically detectable tumor in a patient, there must be selective events during a tumor's evolution that allow it to escape the surveillance of the immune system. Several mechanisms have been proposed for a tumor immune escape including loss of antigenicity (failure to present antigens properly), loss of immunogenicity (failure to induce an immune response by release of immunosuppressive molecules), or recruitment/establishment of an immunosuppressive microenvironment (Clin. Cancer Res. 2015, 21 (4): 687-92 and J. Vet. Res. 2016 60:453-60).

The goal of currently developed immunotherapies is to modify the tumor and its associated microenvironment from immune evasion to immune responsive leading to a productive anti-tumor response (Oncogene 2008, 27 (45): 5868). Strategies often involve activating tumor-specific effector T cells (TEff) by artificially introducing more TEff cells through an allogeneic transplant (Curr. Opin. Hematol. 2015, 22 (6): 509-15), inducing a tumor-specific immune response in the patient via vaccination with a known tumor neoantigen (Immunol. Rev. 2008, 222:357-67), or inhibition of negative T cell regulatory checkpoints like the programmed death-1 (PD-1) or the cytotoxic T-lymphocyte-associated antigen 4 (CTLA-4) signaling pathways (Cancer Control 2014, 21 (3):231-7). These therapeutic strategies have been successful clinically and address several of the mechanisms leading to tumor immune escape. Therapeutic options to modify the immunosuppressive microenvironment have been limited and have been suggested to be needed for improved T cell activation in the tumor (Front. Chem. Sci. Eng. 2017, 12 (4):237). Alternatively to inducing an adaptive immune response to the tumor, activation of the innate immune system is also a recognized strategy to reactive an immune response against the tumor.

CD47 is a cell surface protein that belongs to the immunoglobulin superfamily. It binds several proteins including signal-regulatory protein-alpha (SIRPα) expressed on phagocytic cells of the innate immune system like macrophages. Binding of CD47 to SIRPα leads to inhibition of phagocytosis. In this respect, CD47 plays a critical role as a "don't eat me" signal for phagocytic cells, making cells expressing CD47 resistant to phagocytosis. CD47 is widely expressed at low levels on a majority of normal cells. However, CD47 was also found to be overexpressed on many tumors providing additional shielding from surveillance by the immune system and leading to an escape from destruction by the innate immune system. One method to disarm the "don't eat me" signal on cancer cells is to block CD47 with small molecules or antibodies that prevent engagement of the CD47-SIRPα signaling cascade. This approach has been demonstrated for several hematologic and solid malignancies including lymphoma, brain cancer, breast cancer, ovarian cancer, and small cell lung cancer (Eur. J. Cancer 2017 76:1100-109). Several of these studies demonstrated that blockade with a CD47 monoclonal antibody (mAb) not only inhibited the growth of the primary tumor but prevented the formation of metastatic lesions. Although CD47 is expressed on both normal and cancer cells, antibodies blocking CD47 selectively target cancer cells and not normal tissues. The mechanism for this selectivity has not been completely elucidated, but evidence suggests that healthy cells lack a secondary pro-phagocytic "eat me" signal and are not subject to phagocytosis by macrophages (Proc. Natl. Acad Sci USA. 2012, 109: 6662-67). Human clinical trials are currently ongoing for several solid and hematologic malignancies using various CD47 monoclonal antibodies and results demonstrate a favorable safety profile with transient mild to moderate toxicities. CD47 therapy was also demonstrated efficacy in canine lymphoma and suggests translation of CD47-based therapies into veterinary patients (Cancer Immunol. Res. 2016, 1072-1087).

Immunotherapies for Cancer Therapy. Passive immunotherapy with mAbs have become the standard of care for many human diseases including several types of cancers. Combined sales of mAb products is expected to be nearly $125 billion by 2020 (mAbs 2015, 7:9-14) and is continued to grow at a rate of ~4 new products per year. One of the major concerns with monoclonal antibody therapy is their very high cost with the average cost for treatment approaching ~$50/mg with a conservative estimate of ~$54,000 per patient over a 12-week treatment schedule. Depending on the dosing schedule, costs for monoclonal antibody therapies can quickly reach $1 million per patient per year (Am Health Drug Benefits 2015, 8:9). The overall costs of mAb-based therapies is not just prohibitive for many individuals, but there is evidence that it might not be sustainable for the society (Health Economics 2015, 8:9).

An alternative to passive immunotherapy, active immunotherapies can be both effective and affordable since immunization does not require infusion of multiple doses of expensive mAbs but stimulates the patient's own body to produce its own antibodies. One example of an active anti-cancer therapy is an anti-CD2 immunotherapy for neuroblastoma (Expert Rev. Anticancer Ther. 2017, 17(10): 889-904).

Figure 2:
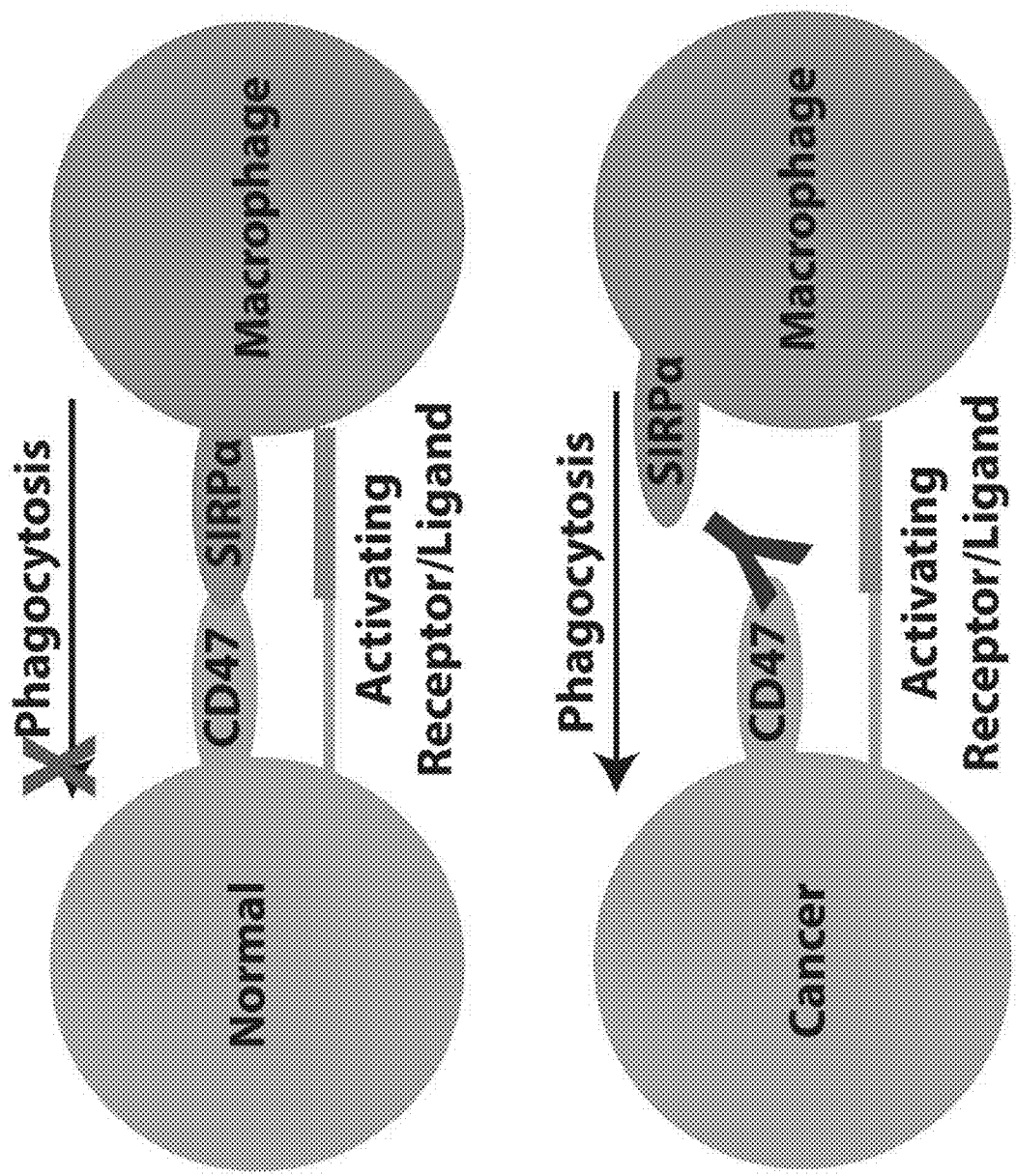
FIG. 2. Schematic illustration of CD47-SIRPα interaction and inhibition of phagocytosis and schematic illustration of blocking of CD47-SIRPα interaction by anti-CD47 blocking antibody and initiation of phagocytosis.

Filamentous Bacteriophages as Platforms for Anti-Cancer Active Immunotherapies. The filamentous bacteriophages (or phages) of the class Ff, which includes fd, fl, and M13, are long, thin viruses of gram negative bacteria consisting of a single-stranded circular DNA genome packed into a cylindrical shell composed of the major coat protein pVIII (98% of total protein by mass) and a few copies of the minor coat protein capping the ends of each particle, as depicted in FIG. 1. Due to the particulate nature and nano-sized scale of the phage virion, they are effectively internalized by phagocytic antigen presenting cells and can stimulate a both humoral and cytotoxic immune responses. Given these physical features coupled with a high particle stability and low cost of production, bacteriophages have become an attractive antigen delivery system for development of various vaccine platforms (J. Immunol. 2008, 108 (6):3719-28). To serve as vaccines, phage viral particles are genetically engineered or chemically conjugated with an antigenic peptide that is then linked to the phage coat proteins and must demonstrate a good safety profile.

Filamentous bacteriophages are non-pathogenic for animals, including humans, and have been used experimentally in humans with the approval of the FDA and in multiple species with no apparent side effects, indicating their safety and tolerability as an immunization platform.

In our previous research project, we successfully used several p3-type phage display libraries to identify 3 lead peptides that have homology to the CD47 molecule and are located between the CD47-SIRPα interaction site. We then demonstrated that these isolated peptides bind to several commercially available anti-CD47 monoclonal antibodies. Next, we tested either genetically modified phages or chemically conjugated peptides to display the selected peptide sequence across the surface of the phage particle. Based on our ELISA results, we obtained more peptides displayed in the correct orientation on the surface of chemically conjugated particles and optimized the peptide linkages used to extend the peptide from the surface of the phage. Three lead CD47-mimicking phage-peptide constructs were identified and are currently being testing in dogs for their ability stimulate production of anti-CD47 neutralizing antibodies.

Objectives

The long-term goal of this research program is to generate effective phage-based platforms for active immunization against CD47, a molecular target that is widely used for development of immunotherapies against several types of human and canine cancers. We hypothesize that active immunization against CD47 using the CD47-mimicking phage-peptide constructs will stimulate production of neutralizing CD47 antibodies that produce blocking of the CD47-SIRPα signaling axis and will ultimately enable activation of the innate immune response to remove cancer cells overexpressing CD47. To prove this hypothesis, we seek to test the following three specific aims in the scope of this project. Specific Aim 1: CD47 is overexpressed in several types of canine cancer, Specific Aim 2: immunization of CD47-mimicking phage-peptide constructs in a mouse model with an established melanoma tumor will produce a reduction in tumor volume (therapeutic response), and Specific Aim 3: immunization of CD47-mimicking phage-peptide constructs in a mouse model prior to engraftment of a melanoma tumor will prevent growth in tumor volume and provide protection against tumor formation (prophylactic response).

At the completion of this study, we anticipate validation of several assays for analyzing and describing CD47 expression in several canine cancer types from cell culture and FFPE tissue archives. We also plan to test three CD47-mimicking phage-peptide constructs for their ability to induce neutralizing antibodies against CD47 and prevent tumor growth/establishment in a mouse allograft model of melanoma. Following this study, we will be in an ideal position to translate our findings into a clinical trial in a canine population for multiple cancer types identified through our work. This research will develop novel active anti-cancer immunotherapies that will be inexpensive (as opposed to the costly monoclonal antibody therapies Approach, Methods, Design Specific Aim 1: CD47 is Overexpressed in Several Types of Canine Cancer. To analyze the gene expression and protein expression profiles of CD47, we will use a panel of canine mammary cancer cell lines isolated and characterized by Dr. Bird's lab in comparison with phenotypically normal breast epithelial cells or normal fibroblasts. Cells will be cultured using standard culture methods routinely performed in the Bird lab. Cells will be maintained in the appropriate cell culture medium in a 37° C. incubator with 5% CO2 until cells are ~70-80% confluent. Cells will then be passaged as normal and total RNA extracted using a Qiagen RNeasy Kit according to the manufacturer's recommendations. RNA quality, purity, and concentration will be assessed by UV/Vis spectroscopy and gel electrophoresis. cDNA will be synthesized using a Promega 1-step RT-qPCR kit and CD47 transcripts will be amplified using a SYBR-Green Master Mix containing CD47-specific primers (J. Cell Sci. 1995. 108: 3419-25) with subsequent normalization against 2-3 standard housekeeping genes (GAPDH, TBBP, etc.). To analyze protein expression, we will perform flow cytometry with a commercially available anti-CD47 antibody. Briefly, cells will be collected by mild trypsinization or scraping of the cell monolayer and resuspending in 1×PBS before fixation with paraformaldehyde. Cells will be blocked before labeling with an anti-CD47 antibody and an appropriate secondary antibody following titration/optimization of ideal antibody dilutions. Labeled cells will be passed through a 40 μm nylon mesh before being analyzed for fluorescence by flow cytometry.

To analyze the protein expression of CD47 in the context of tissues, we will perform a retrospective analysis of archived materials from the AUCVM Pathobiology FFPE tissue archive to identify relevant cases receiving a cancer diagnosis and have an associated patient history available for complete description of the sample. Ideally, cancer cases with adjacent tissue or other non-cancerous lesions would be preferred to demonstrate overexpression of CD47 specifically in the tumor tissues. Formalin-fixed, paraffin-embedded (FFPE) tissues will be cut using standard procedures developed by the histology lab and mounted on charged, glass slides. Slides will be stained with Hematoxylin and Eosin (H&E) or CD47-specific IgGs with a Hematoxylin (nuclear) counterstain following optimization of reaction conditions including antibody dilutions, antigen retrieval, and incubation times. Slides will be digitally archived using an Aperio ScanScope CS and a level of expression determined by a study-blinded anatomic pathologist.

Expected outcomes and potential pitfalls: We expect to analyze the CD47 mRNA and protein expression from at least 5 different canine mammary cancer cell lines and analyze the CD47 protein expression in at least 10 different canine patients receiving a positive cancer diagnosis as confirmed by a pathologist. There is a manuscript describing CD47-specific primers for each of the 4 isoforms of CD47 mRNA. However, these primers may not work using our reaction conditions or with the canine mRNA samples and may require design/construction of new primers. Dr. Bird and I have extensive experience designing target-specific primers for qPCR analysis and does not pose any significant problem to complete the study as planned. Similarly, there is no known anti-CD47 antibody with demonstrated binding to canine mammary cancer cells or canine tissue samples by IHC. We will have to test several antibodies and optimize reaction conditions until a suitable antibody and dilutions are found. Given the high homology of the CD47 protein sequence to the human reference, we do not expect binding specificity to be a major issue. Dr. Cattley has extensive experience optimizing new IHC assays for clinical diagnostics and does not pose any significant problem.

Specific Aim 2: Immunization of CD47-Mimicking Phage-Peptide Construction with an Established Melanaoma Tumor with Product a Therapeutic Response. CD47-mimicking phage-peptide constructs will be prepared as in our previous procedures. Briefly, M13 bacteriophage vector will be amplified in bacteria and purified using standard double PEG precipitation procedures (Curr. Protoc. Protein Sci. 2008; Chap 18: Unit 18.9). Phage purity and concentration will be estimated in virions per mL by absorbance spectroscopy on a NanoDrop 2000 UV/Vis spectrophotometer. CD47-mimicking peptides will be synthesized by a commercial supplier to ensure high quality and purity of products. Peptides will be linked to purified phages using either EDAC or Sulfo-SMCC chemistries and allowed to react for 0.5-5 hours at room temperature. Phage-peptide constructs will be purified using dialysis or a desalting column and eluted in sterile 1×PBS, pH 7.2 buffer. The stability of constructs has not been studied at this time and will be prepared fresh before injections.

To develop the mouse melanoma tumor model (10 mice), B16-F0 cells (~5×105 cells in 1×PBS) will be injected subcutaneously into the flank of C57BL/6J mice obtained from The Jackson Laboratory (JAX, Bar Harbor, Me.) at 6-10 weeks of age. B16-F0 tumors will grow equally in male and female mice, but sex-dependent differences were observed in tumor immunity and their response to immunotherapies. Therefore, to compare for differences based on gender, tumor growth and immunization studies will be studied in both genders. Based on previous experience with other tumor models and from literature data, it is expected that tumors of suitable mass will be produced in ~3-4 weeks.

To test the ability of CD47-mimicking phage-peptide constructs to produce neutralizing antibodies in an established allograft of cancer, we will test 3 different phage-peptide constructs (10 mice per group) in comparison with an untreated control group receiving 1×PBS. B16-F0 tumors will be implanted into mice as described above at approximately 6-7 weeks of age. Extra mice will be implanted to allow selection of mice that have demonstrated tumor growth before vaccination. After 14 days, mice will be assigned to a treatment group and each mouse will be administered ~1011 virions via subcutaneous injection (~250 μL per side) as performed previously (J. Biotech. 2015, 216:20-28). Animals will be monitored for tumor growth, changes in body weight, or clinical signs of failing health. Tumor volumes will be determined using digital caliper measurements at two dimension and calculated using the volume for an ellipsoid sphere. Blood will be collected from mice prior to immunizations to monitor the development of an antibody response by CD47-specific ELISA assay developed in previous years of the project.

Expected outcomes and potential pitfalls: We expect CD47-mimicking phage-peptide constructs to induce production of neutralizing antibodies which will cause the inhibition or regression of tumor size. Based on the results in our ongoing study with dogs, we will be able to determine a profile for IgG production from the three constructs. Alternatively, several mice without tumors will be used to monitor IgG production by ELISA assay to optimize injection timepoints. Depending on the growth curves produced for the melanoma tumor models, it is also expected that the tumors will grow too fast to elicit production of IgGs. In this case, an injection of CD47-mimicking phage-peptide constructs will be given 1-2 weeks prior to establishing the B16-F0 tumors to allow induction of IgMs and a second booster injection of phage-peptide constructs will be given 2 weeks following administration of tumors to allow class switching and production of CD47-specific IgGs.

Specific Aim 3: Immunization of CD47-Mimicking Phage-Peptide Constructs Prior to Engraftment of Melanoma Tumors Will Provide a Prophylactic Response. CD47-mimicking phage-peptide constructs will be prepared and analyzed as above in Specific Aim 2 and B16-F0 melanoma tumors will be prepared above. To test for a prophylactic response of CD47-mimicking phage-peptide constructs to prevent growth of melanoma tumors, a similar experiment as performed in Specific Aim 2 will be performed. However, in this experiment, mice (10 mice per group) will receive two subcutaneous injections of the appropriate CD47-mimicking phage-peptide construct spaced at 4 weeks apart prior to establishment of the B16-F0 tumor grafts. Control mice will receive two injections of 1×PBS prior to establishment of the tumor grafts. All serum collection and data analysis will be the same as in Specific Aim 2 described above.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. An isolated peptide comprising an amino acid sequence selected from: GLSDYYRALAN (SEQ ID NO:1), GITEYLRTINIG (SEQ ID NO: 2), DYSLRLQYGHTY (SEQ ID NO:3), EYVAPFNFLEWK (SEQ ID NO:5), YSDTSLSYMQRY (SEQ ID NO:6), and GLGDRLSHGHTI (SEQ ID NO:7).

2. An isolated peptide consisting of an amino acid sequence selected from: GLSDYYRALAN (SEQ ID NO: 1), GITEYLRTINIG (SEQ ID NO: 2), DYSLRLQYGHTY (SEQ ID NO:3), GLTDYLG (SEQ ID NO:4), EYVAPFNFLEWK (SEQ ID NO:5), YSDTSLSYMQRY (SEQ ID NO:6), and GLGDRLSHGHTI (SEQ ID NO:7).

3. A conjugate comprising the peptide of claim 1 conjugated to a bacteriophage.

4. The conjugate of claim 3, wherein the peptide is conjugated to the bacteriophage via an amide bond.

5. The conjugate of claim 3, wherein the peptide is conjugated to the bacteriophage via a 4-thio-N-maleimidomethyl-cyclohexane-1-amido linker.

6. A method for preparing the conjugate of claim 4, the method comprising reacting the bacteriophage, the peptide, and a reagent comprising a carbodiimide to form the conjugate.

7. A method for preparing the conjugate of claim 5, the method comprising reacting the bacteriophage and a sulfo-succinirmidyl-4-(N-naleimidotmethyl)cyclohexane-1-carboxylate (Sulfo-SMCC) crosslinker to form a maleimide-activated bacteriophage, and reacting the maleimide-activated bacteriophage with the peptide to form the conjugate.

8. An immunogenic composition comprising:
  (a) the isolated peptide of claim 1; and
  (b) a suitable excipient, carrier, or diluent.

9. The composition of claim 8, further comprising an adjuvant.

10. A method for producing an immune response against CD47 in a subject in need thereof, the method comprising administering the immunogenic composition of claim 8 to the subject.

11. A method for producing an immune response against CD47 in a subject in need thereof, the method comprising administering an immunogenic composition comprising the conjugate of claim 3 and a suitable excipient, carrier, or diluent to the subject.

12. A method for treating a subject having a cancer that expresses CD47, the method comprising administering an effective amount of the composition of claim 8 to the subject for treating the cancer.

13. A method for treating a subject having a cancer that expresses CD47, the method comprising administering an effective amount of an immunogenic composition comprising the conjugate of claim 3 and a suitable excipient, carrier, or diluent to the subject for treating the cancer.

14. An isolated polynucleotide that encodes the peptide of claim 1.

15. A mammalian expression vector that expresses the peptide of claim 1.

16. An immunogenic composition comprising:
  (a) the isolated peptide of claim 2; and
  (b) a suitable excipient, carrier, or diluent.

17. The composition of claim 16, further comprising an adjuvant.

18. A method for producing an immune response against CD47 in a subject in need thereof, the method comprising administering the immunogenic composition of claim 16 to the subject.

19. A method for treating a subject having a cancer that expresses CD47, the method comprising administering an effective amount of the composition of claim 16 to the subject for treating the cancer.

* * * * *

UNITED STATES PATENT AND TRADEMARK OFFICE
CERTIFICATE OF CORRECTION

PATENT NO. : 11,666,624 B2
APPLICATION NO. : 17/031663
DATED : June 6, 2023
INVENTOR(S) : Tatiana I. Samoylova et al.

Page 1 of 1

It is certified that error appears in the above-identified patent and that said Letters Patent is hereby corrected as shown below:

In the Specification

Column 1, Line 40, "µlays" should be --plays--.

Column 20, Line 13, "ASO21/ASO2" should be --AS021/AS02--.

Column 26, Line 2, "µlays" should be --plays--.

Column 27, Line 31, "µlays" should be --plays--.

Column 28, Line 47, "$10^3$" should be --$10^{13}$--.

Column 29, Line 39, "µl 120" should be --µl $H_2O$--.

Column 32, Line 47, "µlays" should be --plays--.

In the Claims

Column 65, Claim 7, Line 42, "succinirmidyl-4-(N-naleimidotmethyl)" should be --sulfosuccinimidyl-4-(N-maleimidomethyl)--.

Signed and Sealed this
Twenty-first Day of May, 2024

Katherine Kelly Vidal
*Director of the United States Patent and Trademark Office*